(12) United States Patent
Boeriu et al.

(10) Patent No.: US 11,414,684 B2
(45) Date of Patent: Aug. 16, 2022

(54) PRODUCTION OF FATTY ACID ESTOLIDES

(71) Applicants: Stichting Wageningen Research, Wageningen (NL); Technische Universiteit Delft, Delft (NL)

(72) Inventors: Carmen Gabriela Boeriu, Wageningen (NL); Anamaria Todea, Carei (RO); Isabella Wilhelmina Christina Everdina Arends, Delft (NL); Ludwina Gerharda Otten, Delft (NL)

(73) Assignees: Stichting Wageningen Research, Wageningen (NL); Technische Universiteit Delft, Delft (NL)

( * ) Notice: Subject to any disclaimer, the term of this patent is extended or adjusted under 35 U.S.C. 154(b) by 18 days.

(21) Appl. No.: 17/157,162

(22) Filed: Jan. 25, 2021

(65) Prior Publication Data
US 2021/0207180 A1    Jul. 8, 2021

Related U.S. Application Data

(62) Division of application No. 15/561,644, filed as application No. PCT/EP2016/056656 on Mar. 24, 2016, now Pat. No. 10,920,252.

(60) Provisional application No. 62/138,541, filed on Mar. 26, 2015.

(30) Foreign Application Priority Data

Mar. 26, 2015  (GB) ..................... 1505178

(51) Int. Cl.
| | |
|---|---|
| C12N 9/88 | (2006.01) |
| C12P 7/6436 | (2022.01) |
| C12P 7/64 | (2022.01) |
| C12P 7/42 | (2006.01) |
| C12N 9/20 | (2006.01) |
| C11C 1/00 | (2006.01) |
| C12P 7/6418 | (2022.01) |

(52) U.S. Cl.
CPC ............ *C12P 7/6436* (2013.01); *C11C 1/002* (2013.01); *C12N 9/20* (2013.01); *C12N 9/88* (2013.01); *C12P 7/42* (2013.01); *C12P 7/64* (2013.01); *C12P 7/6418* (2013.01); *C12Y 402/01053* (2013.01)

(58) Field of Classification Search
CPC .... C12N 9/88; C12N 9/20; C12P 7/42; C12Y 402/01053
See application file for complete search history.

(56) References Cited

U.S. PATENT DOCUMENTS

| | | |
|---|---|---|
| 5,082,769 A | 1/1992 | Miki et al. |
| 7,498,454 B2 | 3/2009 | Redlingshoefer et al. |
| 2013/0040340 A1 | 2/2013 | Dauner et al. |
| 2013/0102041 A1 | 4/2013 | Aguieiras et al. |

FOREIGN PATENT DOCUMENTS

| | | |
|---|---|---|
| EP | 2757158 A1 | 7/2014 |
| JP | S6416591 A | 1/1989 |
| JP | S6416592 A | 1/1989 |
| JP | 3157028 U | 1/2010 |
| WO | 2008119735 A1 | 10/2008 |
| WO | 2016151115 A1 | 9/2016 |

OTHER PUBLICATIONS

Alejandro Arce-Rodriquez, et al., "Non-invasive, ratiometric determination of intracellular pH in *Pseudomonas* species using a novel genetically encoded indicator", Microbial Biotechnology, 12, 799-813, 2019.
"Increasing operational stability of oleate hydratase by immobilization" Abstract_ProtStab2014_CG Boeriu 2014.
"Estolides Synthesis Catalyzed by Immobilized Lipases" Aguieiras et al (2011) Enzyme Res Article ID.432746.
"Oleate Hydratase Catalyzes the Hydration of a Nonactivated Carbon-Carbon Bond" Severs et al. (Aug. 2009) J. Bacteriol. 191 5010-5012.
"Influence of the operating conditions on lipase-catalysed synthesis of ricinoleic acid estolides in solvent-free systems" Bodalo et al. (2009) Biochem Eng. J. 44 214-219(52495481).
"Synthesis and physical properties of mono-estolides with varying chain lengths" Cermak & Isabell (2009) Ind. Crop Products.
"Plant oils: The perfect renewable resource for polymer science?!" De Epinosa & Meier (2011) European Polymer J.
"Enzymes as biocatalysts in the modification of natural lipids" F. D. Gunstone (1999) J. Sci. Food Agr 79 12 1535-1549.
"Oxydation of oleic acid to (E)-10-hydroperoxy-8-octadecenoic and (E)-10-hydroxy-8-octadecenoic acids by *Pseudomonas* sp. 42A2" Guerrero et al. (1997) BBA 1347, 75-81.
"Lipase-Catalyzed Synthesis and Properties of Estolides and Their Esters" Hayes and Kleiman (1995) JAOCS 72, 1309-1316.
"Production of oxygenated fatty acids from vegetable oils by *Flavobacterium* sp. strain DS5" Heo et al. (2009) New Biotech. 26, 105-108.
"Immobilized *Staphylococcus xylosus* lipase-catalysed synthesis of ricinoleic acid Esters" Horchani et al. (2012) J. Mol. Catal. B Enzym. 75 35-42.
"Biotechnology for fats and oils: new oxygenated fatty acids" Hou (2009) New Biotech. 26, 2-10.

(Continued)

*Primary Examiner* — Tekchand Saidha
(74) *Attorney, Agent, or Firm* — Banner & Witcoff, Ltd.

(57) ABSTRACT

It has been found that esterification of a hydroxy-fatty acid by a lipase can be coupled with oleate hydratase (OHase) generation of that hydroxy-FA from an unsaturated FA with a cis C9-C10 double bond, e.g. oleic acid, in a single aqueous buffered reaction medium at low temperature, e.g. 30° C. A simple one-pot enzymatic method to produce fatty acid estolides from one or more triglycerides, e.g. starting from a natural plant oil, is thereby enabled in which the same lipase catalyses both the initial hydrolysis of triglyceride and the final esterification step.

2 Claims, 11 Drawing Sheets

(56) References Cited

OTHER PUBLICATIONS

"Biochemical characterization and FAD-binding analysis of oleate hydratase from Macrococcus caseolvticus" Joo et al. (2012) Biochimie 94, 907-915.

"Production of 10-hydroxystearic acid from oleic acid by whole cells of recombinant *Escherichia coli* containing oleate hydratase from Stenotrophomonas maltophilia" Joo et al. (2012) J. Biotechnol. 158, 17-23.

"Immobilization of Rhizopus oryzae Lipase on Magnetic Fe304-chitosan Beads and Its Potential in Phenolic Acids Ester Synthesis" Kumar et al. (2013) Biotechnol. Bioprocess Eng. 18, 787-795.

"Production of IO(S)-hydroxy-8(E)-octadecenoic acid mono-estolides by lipases in non-aqueous media" Martin-Arjol et al. (2013) Process Biochemistry 2013.

"Biochemical Characterization of the Oxygenation of Unsaturated Fatty Acids by the Dioxygenase and Hydroperoxide Isomerase of Pseudomonas aeruginosa 42A2" Martinez et al. (2010) J. Biol. Chem. 285-9339-9345.

"Natural Estolides Produced by *Pseudomonas* sp. 42A2 Grown on Oleic Acid: Production and Characterization" Pelaez et al (2003) JAOCS 80 859-866.

"Hydrolysis of Oils by Using Immobilized Lipase Enzyme: A Review" Ramachandra et al. (2002) Biotechnol Bioprocess Eng. 7, 57-66.

"Production of a novel compound, 10,12-dihydroxystearic acid from ricinoleic acid by an oleate hydratase from Lysinibacillus fusiformis" Seo et al. (2013) 97,8987-8995.

"The Microbiological Production of 10-Hydroxystearic Acid from Oleic Acid" Wallen et al. (1962) Arch. Biochem. Biophys. 99, 249-253.

"Enzymatic Synthesis ofEstolides by a Bioreactor" Yoshida et al. (1997) JAOCS 74, 261-267.

Search Report for GB1505178.2 dated Dec. 17, 2015.

"The Catalytic Activity of Lipases Toward Hydroxy Fatty Acids—A Review" Hayes (1996) J Am Oil Chemists vol. 73, No. 5.

"Production of 10-hydroxystearic acid from oleic acid and olie oil hydrolysate by an oleate hydratase from Lysinibacillus fusiformis" Kim et al. (2012) Appl Microbial Biotechnol 95:929-937.

D.N. Tran et al. "Perspective of Recent Progress in Immobilization of Enzymes", ACS Catalysis 1:956-968 (Year: 2011).

X. Xiong et al. "Preparation and Characterization of Magnetic Chitosan Microcapsules", Journal of Chemistry Article ID 585613 http://dx.doi.org/10.1155/2013/585613. (Year: 2013).

myristoleic acid (C14)

palmitoleic acid (C16)

oleic acid (C18)

linoleic acid (C18)

alpha linolenic acid (C18)

gamma linolenic acid (C18)

ricinoleic acid (C18)

Conditions: 10 mM Triolein in 20mM phosphate buffer pH 6.5, 30 °C

PRODUCTION OF FATTY ACID ESTOLIDES

RELATED APPLICATION DATA

This application is a divisional of U.S. patent application Ser. No. 15/561,644, filed Sep. 26, 2017, which is the national phase of International Application No. PCT/EP2016/056656, filed Mar. 24, 2016, which claims priority to United Kingdom Application No. 1505178.2, filed Mar. 26, 2015, and to Provisional Application No. 62/138,541, filed Mar. 26, 2015.

FIELD OF THE INVENTION

The present invention relates to production of fatty acid estolides, more particularly estolides derived from oleic acid and other unsaturated fatty acid substrates for oleate hydratase (OHase) which have a cis double bond between C9 and C10. Oleate hydratase converts such substrates to 10-hydroxy fatty acids. Thus oleic acid, one of the most abundant, natural, unsaturated fatty acids, is converted by oleate hydratase to 10-hydroxystearic acid (10-HSA); see FIG. 1. The resulting 10-hydroxy fatty acids can be used to form estolides in which the carboxylic acid functionality of one fatty acid chain forms a secondary ester linkage to the alkyl backbone of another. For example, 10-HSA can form a monoestolide with oleic acid and esters with itself.

It has now been found that formation of such estolides employing 10-HSA and other 10-hydroxy fatty acids can be catalysed by a lipase under aqueous conditions suitable for oleate hydratase activity, i.e. for example in aqueous buffered solution at about pH 6-6.5 and at low temperature, e.g. 30° C. It has further been shown that consequently it is feasible to couple fatty acid estolide formation with oleate hydratase activity on an unsaturated fatty acid substrate, e.g. oleic acid, or both oleate hydratase activity on such a substrate and lipase hydrolysis of a triglyceride, e.g. triolein, in a single reaction mixture whereby the monomers for estolide formation are provided in situ in the reaction mixture. This opens up for the first time the possibility of a simple one-pot enzymatic process to produce esters of 10-hydroxy-fatty acids from natural oils or a purified triglyceride preparation using two enzymes to catalyse three consecutive reactions—a single lipase to catalyse both the hydrolysis of a triglyceride substrate (1st reaction) and ester synthesis (3rd reaction) coupled with a OHase. Fatty acid estolides can advantageously thereby be provided from bio-based feedstock, e.g. natural plant oils, for many industrial applications including use as biodegradable lubricants and coatings and for use in the food and cosmetic industries (Cermak & Isabell (2009) Ind. Crops Products 29, 205-212).

BACKGROUND TO THE INVENTION

Conventional chemical synthesis of fatty acid estolides from unsaturated fatty acids uses high temperatures, generally above 200° C., and an inorganic catalyst such as tin, titanium or sulphuric acid, usually in dry organic media. Such processes can lead to degradation of the ester and undesired side reactions. Additionally, the resulting energy costs are high. With a view to overcoming such problems, attention of researchers has moved to use of lipases as biocatalysts for hydroxy-fatty acid esterification (Martin-Arjol et al. (2013) Process Biochemistry 48, 224-230).

Lipases have long been known for hydrolysing the triglyceride components of oils to release the fatty acid component(s), e.g. release oleic acid from triolein in which glycerol is esterified with three oleic acid chains. Such enzymatic hydrolysis is usually performed in an aqueous solution that is contacted with the oil forming a liquid-liquid dispersion at ambient conditions (typically 35° C. and atmospheric pressure). The lipase catalyses the hydrolysis of the triglyceride component(s) at the interface between the two liquids. The reaction is reversible so that the final composition of the products and the hydrolysis rate depends on the fatty acid concentration in the oil phase and on the glycerol concentration in the water phase. Use of immobilized lipase is also known for this purpose (Ramachandra et al. (2002) Biotechnol. Bioprocess Eng. 7, 57-66). The main constituents of plant oils are triacylglycerols and hence they are recognised as an important renewable source of fatty acids for various synthetic uses through such lipase action (De Espinosa & Meier (2011) European Polymer J. 47, 837-852: 'Plant oils: The perfect renewable resource for polymer science?!').

Though designed by nature to effect hydrolysis of triglycerides, it has also long been recognised that lipases can, under appropriate conditions, promote esterification as required for estolide formation (F. D. Gunstone (1999) J. Sci. Food Agric. 79, 1535-1549). Much research in relation to such lipase use has focused on formation of estolides from naturally-occurring mono-hydroxy-fatty acids such as ricinoleic acid (12(R)-hydroxy-9(Z)-octadecanoic acid). Castor oil has a high percentage of triglyceride containing ricinoleic acid and hence is well known as a source of commercially available ricinoleic acid obtained by conventional saponification.

In 1989, Yamaguchi et al. reported the direct production of fatty acid estolide from castor oil by provision of a lipase in an aqueous dispersion of castor oil at 30-65 wt %. A good yield of estolide was obtained with use of a lipase capable of hydrolysing at the glyceride beta site or a lipase having partial glyceride selectivity, but not with a lipase having selectivity for the glyceride alpha site. The relevant studies are reported in published Japanese patent applications JPS64-16591 and JPS64-16592. However, such estolide formation relying on the C12 hydroxy group of naturally-occurring ricinoleic acid is not suggestive of lipase-catalysed estolide formation from any C10 hydroxy-fatty acid under conditions compatible with function of an oleate hydratase to provide the hydroxy-FA in situ. Yamaguchi et al. had no need to consider maintaining activity of an oleate hydratase and were limited to consideration of oils that contain a high amount of ricinoleic acid. Moreover, later work of the same group focused on use of immobilised lipase for estolide formation from the same hydroxy-FA; they suggested as preferable use of immobilized *Candida rugosa* lipase on a ceramic carrier with removal of water to carefully control the water content in the reaction environment; see Japanese Patent no. 3157028 and Yoshida et al. (1997) JAOCS 74, 261-267.

More recently, published European Patent Application no 2757158 (Petroleo Brasileiro SA), and the equivalent published US Patent Application US2013102041A, proposed enzymatic synthesis of fatty estolides using an immobilised microbial lipase non-specific for the 1,3-positions of a triglyceride, such as the lipase of *Candida rugosa* or derived from a *Pseudomonas* species, in a solvent-free medium at 70-90° C. and with maintenance of a very low water concentration. Stearic acid and methylricinoleate (biodiesel from castor oil) were employed for estolide formation using the immobilized form of recombinant lipase B of *Candida antarctica* commercially available as Novozyme 435. Similar studies by the same group looking at estolide formation by immobilized lipase from oleic acid and methylricinoleate are discussed in Aguieras et al. (2011) Enzyme Research, Article ID. 432746.

Others have also looked at various operating conditions to improve ricinoleic estolide formation using immobilized lipase in solvent-free systems with emphasis on control of water concentration, e.g. use of molecular sieves to adsorb water and vacuum reaction with air-drying (see for example Bódalo et al. (2009) Biochem. Eng. J. 44, 214-219; Horchani et al. J. Mol. Catal B: Enzym (2012) 75, 35-42). More recently, lipase synthesis of esters of hydroxyl-fatty acids in dry organic solvents such as n-hexane has been proposed (Martin-Arjol et al. (2013) ibid). Such systems are not compatible with any consideration of coupling of lipase-synthesis of fatty acid estolides with oleate hydratase production of hydroxy-FA in the same reaction medium.

Hayes and Kleinman (1995) JAOCS 72, 1309-1316 reports screening of a number of microbial lipases for ability to form estolides from the naturally occurring cis unsaturated hydroxy-FA known as lesquerolic acid (14(R)-hydroxy-11(Z)-eicosenoic acid) and oleic acid in different reaction systems: native lipases in aqueous-organic biphasic medium employing isooctane, immobilised lipase and reverse micelles. The results further support that 'random lipases', i.e. lipases lacking 1,3-positional specificity with respect to triglyceride (for example the lipases of Candida rugosa, Chromobacterium viscosum, Geotrichum candidum and Pseudomonas species) are effective in catalysing estolide formation. In contrast, 1,3-positional specific lipases tested were ineffective (with the exception of Aspergillus niger lipase which provided a small amount of estolide). This accords with such lipases not utilising, or poorly utilising, secondary alcohols as substrate. The product distribution was also found to be dependent on the lipase source. Use of Candida rugosa lipase or Geotrichum lipase gave estolide formation with greater than 80% of the estolide being the monoestolide formed from one lesquerolic acyl group and one octadecanoic acyl group. Pseudomonas sp. lipase gave a very different product mixture including a significant amount of monoestolide with two lesquerolic acyl groups and some diestolide. However, again no information is provided relevant to coupling lipase esterification with formation of a hydroxy-FA by oleate hydratase.

Todea et al (2015) Pure Appl. Chem. 87, 51-58 reported the screening of a number of free and immobilized lipases and an immobilized protease for their capability to synthesize estolides form hydroxy acids with primary and secondary hydroxyl groups, i.e. 16-hydroxyhexadecanoic acid (16-HHDA), 12-hydroxy-9-cis-hexadecenoic acid (ricinoleic acid, RCA), and 12-hydroxy-octadecanoic acid (12-HSA), in dry organic solvents at 60° C. The results showed that non-regiospecific lipases are able to catalyze the synthesis of estolides from both primary and secondary hydroxy-fatty acids; the reactivity of lipases for the tested substrates decreased in the order: C16(16OH)>C18(12OH:9)>C18 (12OH). Most efficient were found to be lipases from Pseudomonas fluorescens, Pseudomonas. stutzeri, C. antarctica B, C. rugosa, Alcaligenes species and Thermomyces lanuginosus. The product distribution depended on the type of substrate and the type of lipase, but the main product in all cases was the monoestolide, representing 60-80% of the product formed. Lipases B from C. antarctica and Pseudomonas lipases produced longer chain estolides including di-, tri- and tetramers, while small amounts of monolactones (i.e. cyclic esters derived from the hydroxy-fatty acid by ring closure) where obtained only with lipase from P. fluorescens and P. stutzeri.

As part of the same studies, various immobilized lipases (lipases as cross-linked enzyme aggregates (CLEA) from P. stutzeri (CLEA-P. stutzen) and C. antarctica B (CLEA CalB) and CLEA Alcalase, T. lanuginosus lipase immobilized on granulated silica (Lipozyme TL) and C. antarctica lipase immobilized on acrylic resin (Novozyme 435) were found to achieve high yields of estolides, when incubated with the same hydroxy-fatty acids at 75° C. for 24 hours in toluene. The main product obtained was the monoestolide. While longer estolides were obtained with all enzymes and 16-HHDA containing a primary hydroxyl group, immobilized enzymes produced only the monoestolide of 12-HSA and ricinoleic acid with the exception of the CLEA-P. stutzeri lipase that produced a mixture of polyestolides up to heptamers for 12-HSA and decamers for ricinoleic acid.

Estolides have been found to be detectable in submerged cultures of Pseudomonas aeruginosa 42A2 when cultivated with oleic acid and when oleic acid is incubated with partially purified lipase obtained from the same Pseudomonas for 72 hours at 30° C. in a Tris buffer medium containing sodium deoxycholate and $CaCl_2$. However, the pH of the reaction medium was 9.2 and such estolide formation has solely been linked with biotransformation of oleic acid to two trans unsaturated hydroxy-fatty acid derivatives by a reaction mechanism unrelated to oleate hydratase (Peláez et al. (2003) JAOCS 80, 859-866; Guerrero et al. (1997) Biochem. Biophys. Acta 1347, 75-81; Martinez et al. (2010) J. Biol. Chem. 285, 9339-9345; Martin-Arjol et al. (2013) Ibid.)

The biotransformation of oleic acid into 10-hydroxystearic acid was first identified in a presumed Pseudomonas strain, designated as strain 3266 more than half a century ago (Wallen et al. (1962) Arch. Biochem. Biophys. 99, 249-25). Due to its properties such as good fluidity at low temperature and good oxidative stability, oleic acid was subsequently successfully tested as a substrate for microbial hydration by a variety of microorganisms including other Pseudomonas sp. strains and species of Nocardia (Rhodococcus), Corynebacterium, Sphingobacterium, Micrococcus, Macrococcus, Aspergillus, Candida, Mycobacterium and Schizosaccharomyces. The product stereospecificity is dependent on the microorganism. For example, mixtures of enantiomers were obtained using Rhodococcus rhodochrous ATCC 12674 and Sphingobacterium, while optically pure 10(R)-HSA resulted by using Pseudomonas sp. NRRL B-3266 (See Hou (2009) New Biotechnology 26, 105-108, 'Biotechnology for fats and oils: new oxygenated fatty acids').

In 2009, Bevers et al. first reported isolation and biochemical characterisation of the oleate hydratase from Pseudomonas strain 3266, re-classified on the basis of sequence information as Elizabethkingia meningoseptica. The coding sequence for the OHase was cloned (GenBank accession no. GQ144652) and expressed in E. coli as an N-terminal His tag protein to investigate the activity of the OHase in different pH buffers. The optimal pH for activity was observed to be around pH 6; at pH 9 no significant activity was observed. The presence of salt (NaCl) was also shown to influence activity. With the method employed for recombinant OHase production, an optimal concentration of 50 mM NaCl was found in 20 mM Tris buffer (pH 8) at 22° C. It was also observed that the specific activity of the enzyme did not change significantly in the presence of 2.5% or 5% isopropyl alcohol.

However, it decreased at isopropyl concentrations higher than 10% (Bevers et al. (2009) J. Bacteriol. 191, 5010-5012).

A recombinantly produced fatty acid hydratase of *Streptococcus pyrogenes* reported in published International Application WO2008/119735 (Georg-August-Universität) was subsequently identified as a homologue of the *E. meningoseptica* OHase (Bevers et al. (2009) ibid). In 0.1M sodium phosphate buffer at pH 7.1 containing 0.1 M NaCl, it was shown at 37° C. to act preferably at the cis-9 double bond of oleic acid but also to be able to convert other unsaturated fatty acids with a cis C9-C10 double bond (palmitoleic acid, linoleic acid and α-linolenic acid) to the corresponding 10-hydroxy-fatty acid.

A number of other microbial oleate hydratases have since been studied as recombinant functional enzymes. For example, Kim et al. (2012) Appl. Microbiol. Biotechnol. 95, 929-937 reports studies on the production of 10-HSA from oleic acid and olive oil hydrolysate using an oleate hydratase of *Lysinibacillus fusiformis* expressed in *E. coli*. The optimal reaction conditions for producing 10-HSA were found to be aqueous buffer at pH 6.5, 35° C., 4% (v/v) ethanol. The hydration activity was shown to be highest for oleic acid but activity was also shown against a number of other unsaturated fatty acids of length C14 to C18 with a cis C9-C10 double bond: myristoleic acid (C14), palmitoleic acid (C16), linoleic acid (C18), α-linolenic acid (C18) and γ-linolenic acid (structures shown in FIG. 2). The same OHase was subsequently shown to act also at the C9-C10 cis double bond of ricinoleic acid under similar conditions (pH 6.5, 30° C., 4% (v/v) methanol) to give the dihydroxy fatty acid 10,12-dihydroxystearic acid (Seo et al. Appl. Microbiol. Biotechnol. (2013) 97, 8987-8995).

Conversion of oleic acid to 10-HSA using whole cells of recombinant *E. coli* expressing a microbial OHase has also been reported. Thus, Joo et al. (2012) J. Biotechnol. 158, 17-23 reports conversion of oleic acid to 10-HSA by recombinant *E. coli* expressing the OHase of *Stenotrophomonas malltophilia* at pH 6.5 and 35° C. with 0.5% (w/v) Tween 40.

The same group has also studied the oleate hydratase of *Macrococcus caseolyticus* obtained by recombinant expression in *E. coli* (Joo et al. (2012) Biochemie 94, 907-915). Maximum activity against oleic acid was observed at pH 6.5 and 25° C. with 2% (v/v) ethanol and 0.2 mM FAD. The hydratase was shown to be FAD-dependent; in the absence of FAD no catalytic activity was observed. Besides the activity to oleic acid, the same hydratase was also found to convert myristoleic acid to 10-hydroxytetradecanoic acid and palmitoleic acid to 10-hydroxyhexadecanoic acid respectively with no by-products. Two reactions were observed when linoleic acid, α-linolenic acid and γ-linolenic acid were used as substrates due to additional hydration at the available cis-12 double bond to give a dihydroxy fatty acid.

Thus linoleic acid gave both 10-hydroxy-12(Z)-octadecanoic acid and 10,13-dihydroxy-octadecanoic acid. α-Linolenic acid gave both 10-hydroxy-12(Z),15(Z)-octadecadienoic acid and 10,13-dihydroxy-15(Z)-octadecenoic acid and γ-linolenic acid gave both 10-hydroxy-6(Z),12(Z)-octadecadienoic acid and 10,13-dihydroxy-6(Z)-octadecanoic acid.

More recently, the inventors for the present application have reported demonstration of total conversion of oleic acid to 10-HSA using recombinant oleate hydratase of *Elizabethkingia meningoseptica* produced by *E. coli* as either a free enzyme or immobilized (poster presentation at Biotrans 2013). Purified OHase is recognised to be a very unstable enzyme; with simple storage in buffer at 4° C., recombinant oleate hydratase of *E. meningoseptica* has been found by the inventors to lose about 60% of its activity in 7 days. It was also shown however that both the thermal stability and stability with re-use (operational stability) can be significantly enhanced by immobilization. Of especial note was the finding that among various immobilization methods investigated, covalent linkage on to magnetic chitosan composite particles results in particularly effective stabilization during multiple reuses with enzyme recovery by magnetic separation; the covalently bound enzyme preserved 75% of its initial activity after five reuses at 30° C. for 2 hours per cycle. Furthermore, the same immobilized OHase showed improved thermal stability; it retained more than 65% of its original activity after incubation at 50° C. (reported by oral presentation at ProtStab 2014 and Netherlands Chemistry and Catalysis Conference NCCC 2015).

Heo et al. investigated the ability of *Flavobacterium* sp strain DS5 (NRRL B-14859) to directly convert olive oil and soybean oil to oxygenated fatty acids such as 10-ketostearic acid and 10-HSA. Lipase addition to the culture medium was required since no lipase was induced in the bacterial cells. However, no estolide production was observed (Heo et al. (2009) New Biotechnology 26, 105-108).

Hence, in summary there has previously been much study of enzymic conversion in respect of each individual step required to convert a triglyceride such as triolein to one or more fatty acid estolides—(i) lipase hydrolysis of triglyceride to produce one or more unsaturated fatty acids (ii) hydroxylation of unsaturated fatty acid(s) by oleate hydratase and (iii) the esterification of hydroxy-fatty acid(s), again by lipase action. However, it has not previously been taught how to couple use of a lipase with step (ii) so as to enable the conversion of triolein or any other triglyceride containing oleic acid into 10-hydroxystearic acid and esters thereof in a single one-pot reaction process.

SUMMARY OF THE INVENTION

As indicated above, it has now been found that by carrying out the above-noted esterification step with a lipase in an aqueous buffered solution it is possible to integrate this step with both action of an oleate hydratase on an unsaturated fatty acid and lipase hydrolysis of triglyceride to provide that fatty acid substrate in a single reaction medium with high or total conversion of triglyceride and of hydroxy-fatty acid to ester. This means carrying out the lipase esterification step under very different conditions than currently suggested as preferable for such esterification such as use of an immobilized lipase in an apolar reaction medium.

Thus in one aspect, the present invention provides a method for producing one or more esters of one or more hydroxy-fatty acids wherein at least one such hydroxy-fatty acid is a hydroxy-fatty acid obtainable by action of an oleate hydratase on an unsaturated fatty acid substrate with a cis C9-C10 double bond, said method comprising use of a lipase for esterification of said at least one hydroxy-fatty acid in an aqueous buffered reaction medium and under conditions which are compatible with production of said at least one hydroxy-fatty acid in situ by said oleate hydratase.

It will be understood that such conditions do not preclude an increase of temperature and/or pH variation after a period of oleate hydratase activity in the same reaction medium and whereby lipase use may occur under conditions which are not optimal or even favourable for oleate hydratase activity. Where an oleate hydratase and lipase are provided together in the same aqueous reaction medium, then it may however be preferred not to vary the temperature or pH but provide constant aqueous conditions for both activity of the OHase to produce said at least one hydroxy-FA in situ and esterification by the lipase as illustrated by the exemplification (see Examples 1 to 4).

Thus, the reaction medium may be supplemented with said oleate hydratase in the presence of an appropriate unsaturated fatty acid substrate. Advantageously, the reaction medium may be further supplemented by a triglyceride which is hydrolysed by the same lipase as used for the esterification reaction. This provides in the reaction medium the fatty acid substrate for the OHase and thereby enables a one-pot enzymic process for obtaining one or more fatty acid estolides directly from the triglyceride without need for any separation step.

The estolide product may be affected by the reaction conditions. Thus, while all the enzyme steps of such a one-pot enzymic method may be carried out at the same temperature, as indicated above, a two-temperature method is not excluded from consideration in which the temperature is firstly maintained at a temperature suitable for the chosen OHase, e.g. 30-35° C., and then increased to a higher temperature, e.g. to favour synthesis of higher estolide oligomers (longer estolides than dimers) with high conversion. Change of pH with temperature is also not excluded from consideration to influence the final product(s) e.g. to permit lipase action at a pH not optimal for the chosen OHase. However, such change of temperature and/or pH is not essential to the inventive concept which resides in enabling for the first time a one pot enzymic process for converting triglyceride to estolide product.

For example, as indicated above, such a process may provide one or more fatty acid estolides of 10-HSA starting from triolein as shown in the scheme set out in FIG. 3. In this case, the product will comprise, essentially consist of, or consist of one or more fatty acid estolides selected from the monoestolide of 10-HSA with its parent unsaturated fatty acid, i.e. oleic acid, the monoestolide of 10-HSA with itself, and higher ester oligomers of 10-HSA capped or uncapped by oleic acid (see FIG. 4). In some instances, it is conceivable that some cyclic ester may occur as a minor product. However, the lipase and conditions may be chosen so that exclusively open chain estolide(s) are obtained as illustrated by the examples herein.

A method of the invention as discussed above may further comprise extraction of the one or more ester products, e.g. a fatty acid estolide, from the reaction medium or such extraction and further purification and/or incorporation into a composition. One or more ester products of lipase esterification may be reacted to obtain a further product either before or after extraction or after extraction and further purification.

BRIEF DESCRIPTION OF THE FIGURES

The invention will be further described below with reference to the following figures.

DETAILED DESCRIPTION OF THE INVENTION

Figure 1:
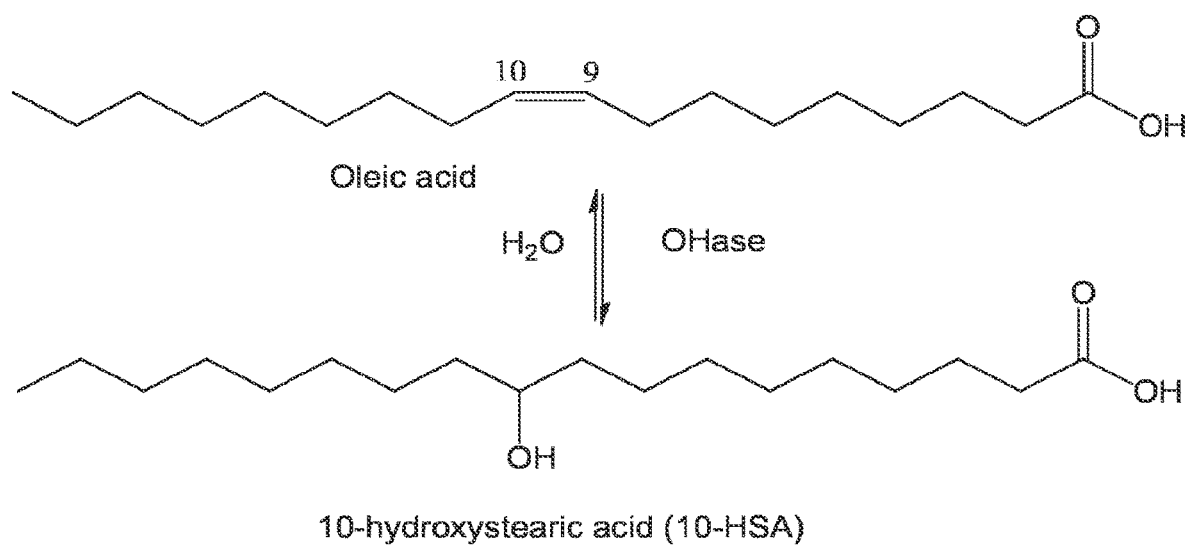
FIG. 1: the hydration reaction of oleic acid catalysed by oleate hydratase to produce 10-HSA.
Figure 2:
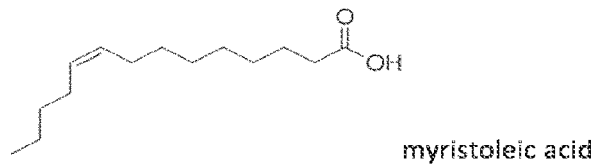
FIG. 2: the structures of examples of unsaturated C14-C18 fatty acids with a cis double bond between C9 and C10 which are known to be substrates for microbial oleate hydratases; monounsaturated fatty acids: myristioleic acid (C14; 9-cis-tetradecanoic acid), palmitoleic acid (C16; 9-cis-hexadecanoic acid), oleic acid (C18; 9-cis-octadecanoic acid); di- or tri-cis unsaturated fatty acids: linoleic acid (C18; cis-9,12-octadecanoic acid),α-linolenic acid (C18; (9Z,12Z,15Z)-octadecatrienoic acid) and γ-linolenic acid (C18; (6Z, 9Z, 12Z)-octadecatrienoic acid); the hydroxyl-fatty acid ricinoleic acid (C18; 12(R)-hydroxy-9 (Z)-octadecanoic acid).
Figure 2:
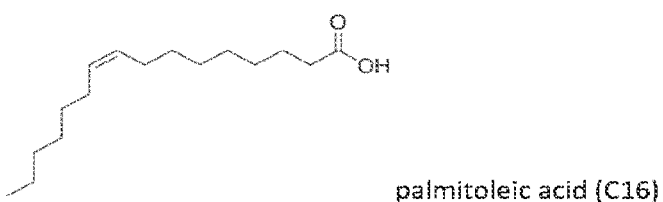
Figure 2:
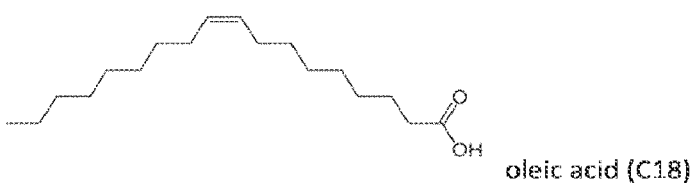
Figure 2:
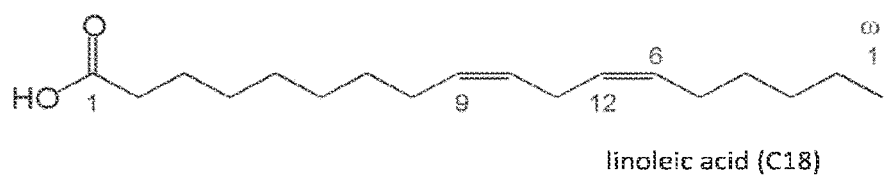
Figure 2:
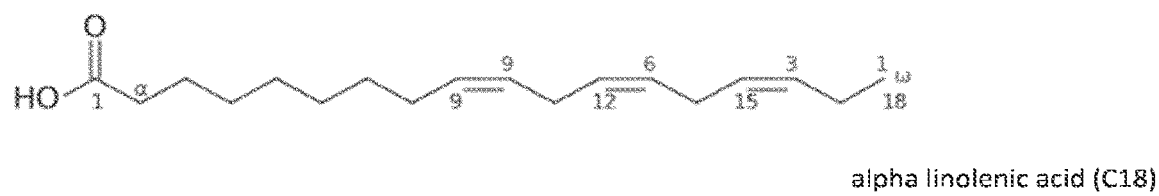
Figure 2:
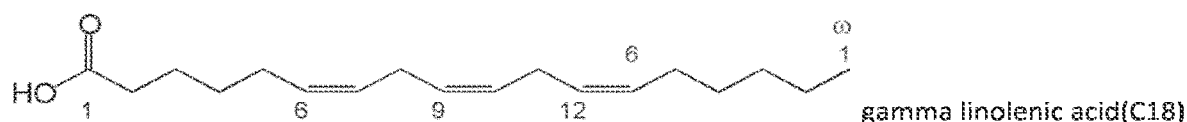
Figure 2:
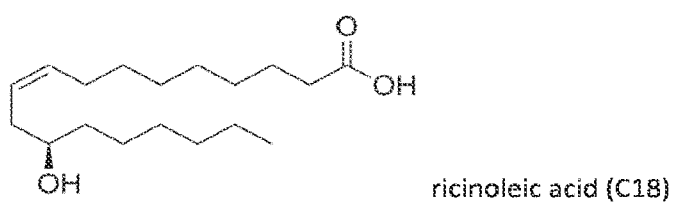

As indicated above, the invention enables fatty acid estolide formation in an aqueous environment, at low temperature and ambient pressure without the need for separation and purification of intermediate products. It enables the integration of three consecutive reactions catalysed by only two enzymes in a single reaction medium for deriving fatty ester estolides from triglycerides which are known to form a high percentage of the lipid content of natural plant oils. It thus allows the production of high value compounds from bio-based feedstock with high efficiency and low energy cost.

Reaction Conditions

As noted above, the reaction conditions may be chosen to be fully compatible with activity of an oleate hydratase to convert an unsaturated fatty acid substrate to the corresponding hydroxy-fatty acid in the same aqueous medium. In this case, generally the reaction medium will comprise an aqueous buffered solution at about pH 8.0, or at about pH 6-8 or at about pH 6 to 6.5. The optimum pH will be influenced by the chosen OHase and whether it is immobilized or not. In some instances, the OHase may show two distinct maximum activity values at about pH 6-6.5 and about 8.0; in others the OHase may exhibit a single optimum activity at about pH 8.0 or about pH 6-6.5 (see Example 8). For example, the reaction medium may preferably comprise a simple aqueous buffer solution at about pH 6.5, e.g. a simple phosphate buffer at pH 6.5. In some instances, it may however be chosen to permit operation of the lipase at a different pH following a period of operation of the OHase. This will generally be within the range of about pH 4 to 8, for example following a period of operation of the OHase, e.g. 24 hours, the pH may be lowered to about pH 6.5 or lower, e.g. about pH 4, to influence the products derived from the hydroxyl-FA(s) produced in situ by OHase activity.

The medium may preferably contain NaCl to improve the activity of the OHase, e.g. at a concentration up to about 150-200 mM, e.g. at about 150 mM or at about 40 to 150 mM, about 40 to 100 mM, about 40 to 60 mM or about 50 mM. The optimum concentration may again vary with the precise nature of the OHase employed. With the purified recombinant OHase of E. meningoseptica employed for the exemplification herein, NaCl at 150 mM was found to be favourable (see Example 1).

As indicated above, a temperature may be chosen to be consistent with both OHase activity and function of the lipase for esterification and hydrolysis of triglyceride. Thus a chosen single reaction temperature may be between about 10 and 50° C., preferably between about 20 and 40° C. Hence, the chosen temperature may generally be about 30-37° C. or about 30-35° C. A temperature of about 30° C. may be chosen. Thus for example an aqueous medium at about pH 6-8 and about 20-40° C. may be conveniently employed, e.g. at about pH 6.5 and about 30° C. as illustrated by the exemplification. However, if enzymes with a high thermal stability are used reaction temperatures above 50° C. may be possible, e.g. a temperature of 60° C. or even 75° C. When enzymes with different thermal stability are used, i.e. an oleate hydratase with lower thermal stability than that of the lipase, a step-increase of the temperature may be used, i.e. starting at a lower temperature suitable for OHase activity, e.g. 30° C. for a period of for example 24 hours, followed by increasing the temperature, e.g. to 60° C. for a period of for example another 24 hours.

The reaction medium may be additionally supplemented with one or more additives, e.g. to aid oleate hydratase activity in the reaction medium, e.g. FAD for an FAD-dependent OHase such as the OHase of Macrococcus caseolyticus. A low amount of an organic solvent, generally lower than 4-5% v/v, may be added to increase the solubility of the hydroxy-FA, e.g. 10-HSA. The solvent should not inhibit the enzymes and must be miscible with the substrates (e.g. triolein and oleic acid) and the products.

One or more monomers may be included in the reaction medium for esterification which supplement the at least one hydroxy-FA derived from an oleate hydratase substrate and any such substrate remaining in the reaction medium. Such additional monomers may for example be non-fatty acid monomers capable of esterification by the lipase to the hydroxy group of a hydroxy-FA. They may be a fatty acid monomer. One or more saturated fatty acids may be added to cap estolide formation from hydroxy-FA monomer(s). However, commonly the monomers available for the lipase esterification step will be restricted to the hydroxy-FA product(s) of oleate hydratase activity and the parent cis-9 unsaturated fatty acid(s), e.g. 10-HSA and oleic acid, 10-hydroxyhexadecanoic acid (10-HHDA) and palmitoleic acid and 10-hydroxy-12-undecenoic acid (10-HUDA) and linoleic acid.

Where a triglyceride is added to the aqueous reaction medium for lipase hydrolysis, the two liquid phases will desirably be mixed thoroughly to form an emulsion. This may be achieved by spinning, e.g. at about 1000 rpm, to aid dispersion of the triglyceride oil phase in the aqueous reaction medium.

The reaction may be stopped by addition of acid and the fatty acid ester product(s) extracted using an organic solvent e.g. dichloromethane. The thus extracted product(s) may be analysed by MALDI-TOF-MS. In this way, the reaction may be monitored and the enzymes and/or conditions and/or time of reaction varied to influence the ester product(s). It will be appreciated that the process of the invention is highly versatile and the starting compounds and conditions may be varied to direct the process to the obtaining of a wide range of desired ester products.

The Ester Product(s)

The product or products of the lipase esterification step will be restricted by the available monomers for esterification. Generally, the esters will be one or more fatty acid estolides consisting solely of fatty acid monomers. Thus as noted above, where a parent mono-hydroxy-FA, e.g. 10-HSA, is provided in situ by the action of an oleate hydratase, any of the following fatty acid estolides may be obtained: the monoestolide of the hydroxy-FA with its parent unsaturated fatty acid, the monoestolide of the hydroxy-FA with itself, and higher ester oligomers of the hydroxy-FA capped or uncapped by the parent unsaturated fatty acid.

Chemical hydroxylation of unsaturated fatty acids is difficult and frequently di-hydroxy derivatives are obtained. In carrying out a process of the invention, it may be desirably ensured that solely one or more mono-hydroxy-fatty acids are generated in situ for esterification. This will simplify the possible ester products. Thus in a preferred embodiment of the invention where only one or more mono-hydroxy fatty acids are provided in the reaction medium for lipase esterification, the possible fatty estolide products may be restricted to one or more fatty acid estolides selected from a monoestolide of a hydroxy-FA with an unsaturated fatty acid, e.g. its parent cis-9 unsaturated fatty acid, a monoestolide of a hydroxy-FA with itself or another hydroxy-FA, and higher ester oligomers formed from one or more hydroxy-FAs capped or uncapped by a non-hydroxy unsaturated fatty acid.

Thus if triolein is provided as the sole starting triglyceride for a process of the invention, solely oleic acid will be provided by lipase hydrolysis of the triolein as substrate for the oleate hydratase. The oleate hydratase will in turn generate solely 10-HSA. As noted above, this restricts the possible open chain estolide products to the monoestolide of 10-HSA with oleic acid, the monoestolide of 10-HSA with itself, and higher ester oligomers of 10-HSA capped or uncapped by oleic acid. Where a single mono-10 hydroxy FA is provided for esterification, the lipase and conditions may be chosen to limit the estolide product solely or essentially solely to monoestolide product.

Figure 4:
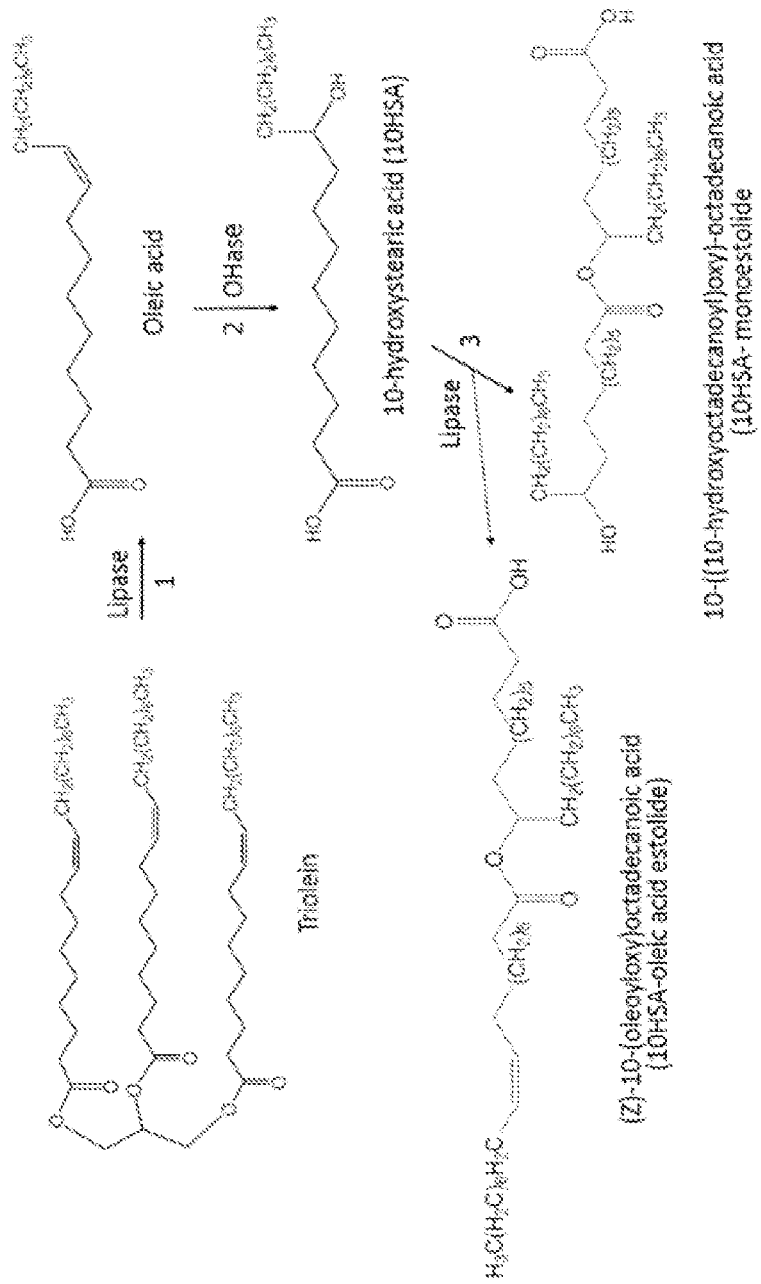
FIG. 4: Estolide formation in a one pot process of the invention where the monomers available for lipase esterification are oleic acid and 10-HSA

Thus, the product distribution may be affected by the kinetics of each reaction and factors including the choice of lipase and the ratio of lipase to OHase. For example, it may be arranged that the only, or essentially the only, ester product generated is monoestolide of an unsaturated fatty acid provided as substrate for the OHase and the mono-hydroxy-FA resulting from action of the OHase on that substrate, e.g. the monoestolide of oleic acid with 10-HSA (see Example 1 using the lipase of Candida rugosa and FIG. 4). Alternatively, a process of the invention with the same starting triglyceride may provide solely or essentially two different monoestolides: the monoestolide of a mono-hydroxy-FA with itself, e.g. the monoestolide dimer formed from two 10-HSA chains, and a monoestolide of that hydroxy-FA with its parent cis-9 unsaturated fatty acid (see Example 2 illustrating use of the lipase of a *Pseudomonas* species and FIG. 4).

It will be recognised however that a variety of estolide products may be achieved. For example, as will be expanded upon below, a broad range of lipases from different sources have been found to be able to catalyze the synthesis of 10-HSA estolides and the choice of lipase and precise conditions of lipase use can influence the nature of the estolides attained. For example, in an aqueous system at pH 6.5 and at 40° C., lipase from *P. fluorescens* has been found to synthesise mono- and di-estolides of 10-HSA, with about 20% conversion, in 24 hours. Increasing the temperature to 60° C., polyestolides up to 15 mers have been found to be obtainable and conversion increases to 70%. As indicated above, it is contemplated that such estolide formation might be combined with use of an OHase at lower temperature, e.g. at 30-35° C., to favour production of 10-HSA from oleic acid followed by a rise of temperature to 60° C. for esterification. However, alternatively with an OHase of higher thermostability (due to immobilization and/or microbial source) polyestolides higher than dimers may be achievable from a cis-9 unsaturated fatty acid in a constant temperature process according to the invention, e.g. operation at 50-60° C.

Choice of Lipase

Any lipase may be employed which will act at the secondary —OH group of 10-HSA to form an ester bond. Such a lipase may be selected from the many lipases that have previously been shown to act at secondary —OH groups of naturally occurring hydroxy-FAs such as ricinoleic acid and lesquerolic acid. Desirably the lipase may be a microbial lipase; it may be a recombinant lipase.

Based on previous studies of lipases for esterification of hydroxy-FAs, generally the chosen lipase will be a non-1,3 positional specific lipase with respect to triglyceride hydrolysis. It may be a non-specific lipase with no positional specificity with respect to triglyceride hydrolysis. By way of example, non-specific lipases from the following fungal and bacterial species may be employed: *Candida* species, e.g. *Candida rugosa, Candida antarctica, Candida lipolytica, Chromobacterium* species, e.g. *Chromobacterium viscosum, Geotrichum* species, e.g. *Geotrichum candidum, Pseudomonas* species, e.g. *Pseudomonas fluorescens,* and *Pseudomonas stutzeri, Alcaligenes* species, *Thermomyces* species, e.g. *Thermomyces lanuginosus; Thermoanaerobium brockii, Aspergillus oryzae, Rhizopus arrhizus* and *Mucor javanicus.* For example, the lipases of *C. rugosa, P. fluorescens* and *P. stutzeri* have been shown by the inventors to be suitable, are commercially available and may therefore be conveniently used.

The estolide synthesis can also be performed with immobilized lipases that can be easily removed from the reaction mixture and reutilised for a number of reaction cycles. Lipases immobilized using different immobilization methods such as adsorption, ionic binding, affinity, hydrophobic interaction, covalent binding, membrane encapsulation, gel entrapment and crosslinking are useful. Such lipases are known in the art and again are commercially available as noted above.

As indicated above, it is recognised that choice of lipase will be a factor which may influence the product distribution. For example, the lipase of *Candida rugosa* may be employed where the desire is to favour production of monoestolide between a hydroxy-FA, obtained or obtainable by action of an oleate hydratase, and its parent unsaturated FA (see Example 1).

Choice of Oleate Hydratase

Where an oleate hydratase is employed to produce a hydroxy-FA in situ in the reaction medium it will preferably be a recombinant oleate hydratase. As indicated above, the coding sequences for a number of microbial oleate hydratase enzymes have previously been cloned and may be readily identified. For example, it may be preferred to use recombinantly produced oleate hydratase of *Elizabethkingia meningoseptica.* As noted above, the coding sequence for that OHase has previously been deposited in GenBank and it may be readily expressed in *E. coli,* e.g. with a His-tag to aid purification.

Use of Immobilized OHase

Figure 8:
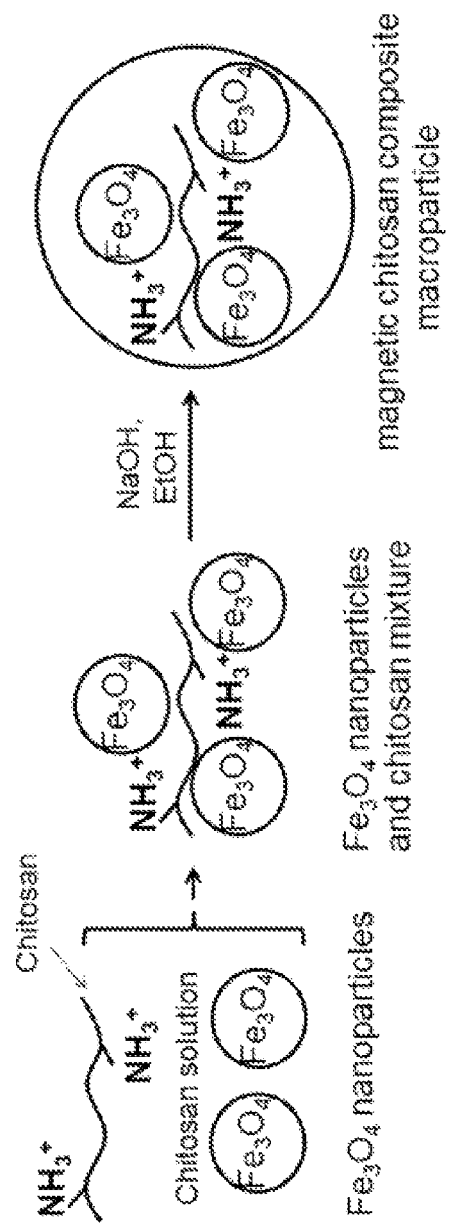
FIG. 8: Diagram of the formation of magnetic chitosan composite particles for immobilization following glutaraldehyde activation of recombinant OHase with an N-terminal His tag.

As noted above, purified recombinant OHase is recognised to have low stability even at ambient temperatures which limits its reuse in commercial applications. Immobilizing the enzyme is liable to cause loss of activity but may nevertheless be preferred to gain thermal stability and easy removal from the reaction mixture with re-cycling. While various methods for immobilization may be contemplated, studies of the inventors referred to above and now reported in more detail herein (see Example 8) provide foundation for particular interest in recombinant OHase covalently linked to chitosan-coated magnetic particles. Such composite particles in which smaller iron oxide magnetic particles, e.g. about 1 μm in diameter, are dispersed in a chitosan matrix may be conveniently prepared using commercially available magnetic particles such as amino-terminated iron oxide magnetic particles (see FIG. 8). For this purpose, the amino-terminated magnetic particles in water (e.g. at 50 mg/ml) may be dispersed in an acidified chitosan solution, e.g. 2% (w/v) chitosan in 2% acetic acid, at, for example, a chitosan solution: wet magnetic particle ratio of about 5:1 (w/w). For immobilization of recombinant OHase with an N-terminal His tag, the composite magnetic chitosan particles may be activated for covalent linkage of the OHase using glutaraldehyde.

Figure 11:
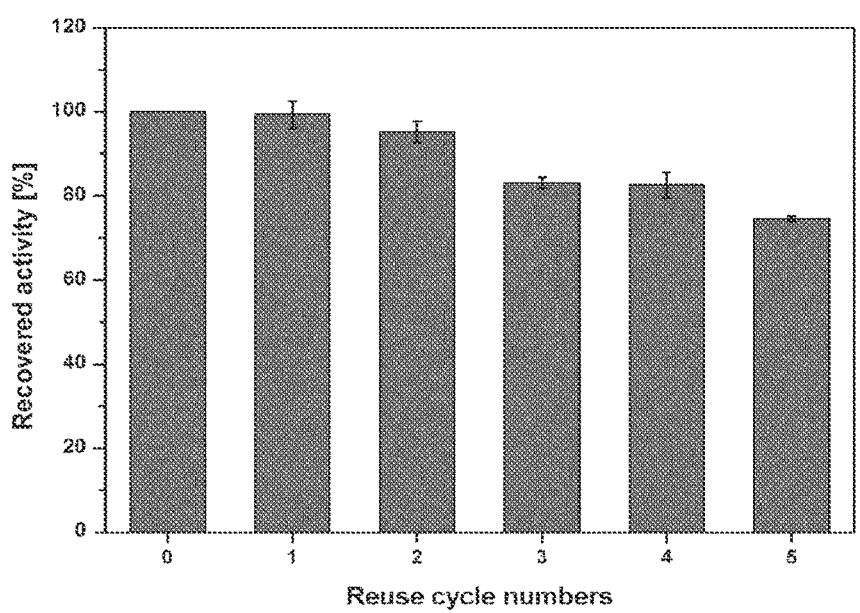
FIG. 11: Variation of activity of OHase immobilized on magnetic chitosan composite particles with multiple re-uses at 30° C. for 2 hours per cycle with enzyme recovery by magnetic separation.

Recombinant OHase of *E. meningoseptica* immobilized in this manner showed adequate recovered activity (higher than achieved with other recognized enzyme immobilization methods; see Table 4 in Example 8) and importantly as noted above, showed very effective improvement of operational stability—the covalently bound enzyme preserved 75% of the initial activity after five reuses at 30° C. for 2 hours per cycle (see Table 2 in Example 8 and FIG. 11). This was accompanied by improved thermal stability. Such immobilized OHase can be readily recovered from a reaction medium by magnetic separation and hence is now contemplated as favourable for use in carrying out methods of the invention with recycling of the OHase to new starting mixtures for batch wise operation.

Provision of Fatty Acid Substrate for an OHase

For a process of the invention, fatty acid substrate for an oleate hydratase may be added to the reaction medium as one or more cis unsaturated fatty acids, e.g. as one or more purified unsaturated cis-9 unsaturated fatty acids or a triglyceride hydrolysate. However, as indicated above, more desirably fatty acid substrate for an OHase will be generated in situ in the reaction medium by hydrolysis of triglyceride by the same lipase as provided for the esterification step.

Thus as a preferred embodiment, the present invention provides a one-pot enzymic method for producing one or more esters of one or more hydroxy-fatty acids wherein at least one such hydroxy-fatty acid is a hydroxy-fatty acid obtainable by action of an oleate hydratase on an unsaturated fatty acid substrate, said method comprising use of a oleate hydratase and a lipase in a single aqueous buffered reaction medium to carry out the following steps without any separation step:

(i) hydrolysis of one or more triglycerides, e.g. triolein, by the lipase to generate one or more unsaturated fatty acids as substrate for said oleate hydratase;

(ii) conversion of said one or more unsaturated fatty acids to one or more hydroxy-fatty acids by said oleate hydratase; and (iii) conversion of said one or more hydroxy-fatty acids by the same lipase to one or more esters.

As indicated above, the reaction mixture will generally be spun to aid dispersion of the triglyceride. Since unsaturated fatty acid, e.g. oleic acid, produced by lipase hydrolysis is immediately converted in the same reaction medium to hydroxy-FA, this favours full conversion of triglyceride.

In the absence of additional monomers in the reaction medium capable of ester bond formation with the hydroxy-FA(s) produced in situ by the OHase, the ester products will be exclusively one or more fatty ester estolides. In the case of provision in the reaction medium of solely one or more mono-10-hydroxy-FAs, it will be appreciated that the possible estolides are any of a monoestolide of a hydroxy-FA with an unsaturated fatty acid, e.g. its parent unsaturated fatty acid, a monoestolide of a hydroxy-FA with itself or another hydroxy-FA, and higher ester oligomers formed from one or more hydroxy-FAs capped or uncapped by a non-hydroxy unsaturated fatty acid.

The one or more unsaturated fatty acid substrates provided for the oleate hydratase may be any unsaturated fatty acid substrate that can be converted by the hydratase to a hydroxy-FA. As indicated above, such substrates are known to include not only oleic acid but other unsaturated fatty acids with a cis double bond between C9-C10. For example, as indicated above, such substrates have been identified as C14-C18 unsaturated fatty acids with a cis-9 double bond, including a number of such naturally-occurring fatty acids. Suitable unsaturated fatty acids may have more than one cis double bond, e.g. at least both a cis-9 and cis-12 double bond in which case as indicated above a dihydroxy fatty acid may be produced with both a C10 and C13 hydroxy group. Suitable unsaturated fatty acid substrates may have exclusively cis double bonds. Thus suitable fatty acid substrates include for example one or more of myristoleic acid, palmitoleic acid, oleic acid, linoleic acid, α-linolenic acid and γ-linolenic acid, all of which are found as fatty acyl components of natural oils.

The OHase of *E. meningoseptica* (EC 4.2.1 53) is strictly specific for a cis C9-C10 double bond. Thus, while other double bonds may be present, a cis C9-C10 bond is considered required in any fatty acid substrate for that enzyme. Thus, particularly if the recombinant OHase from *Elizabethkingia meningoseptica* is used for a one-pot process of the invention, it is considered that a starting triglyceride must contain at least one fatty acid chain with a cis double bond at C9-C10.

As indicated above, generally it will be preferred to provide for esterification only one or more mono-hydroxy-FAs, more preferably a single 10-hydroxy-FA. Thus as indicated above, preferably an OHase in the reaction medium may be solely contacted with oleic acid as its fatty acid substrate and used to provide solely 10-HSA for lipase esterification.

Oleate hydratase and a lipase may, for example, be contacted with triolein, or an oil-comprising triolein, in an aqueous buffered reaction medium suitable for activity of both enzymes, e.g. an aqueous phosphate buffer solution at pH 6.0-6.5 and 30-35° C. containing 50-150 mM NaCl, whereby the following steps occur consecutively without any separation step:

(iv) hydrolysis of triolein to generate oleic acid;

(v) conversion of oleic acid to 10-HSA by the oleate hydratase and (vi) conversion of 10-HSA to one or more estolides by esterification with itself and/or oleic acid, the reaction mixture desirably being continuously spun, e.g. at 1000 rpm for 24-48 hours.

While triolein has a single type of fatty acyl chain, it will be understood that triglyceride(s) provided in the reaction medium for hydrolysis by the lipase may have a glycerol component esterified to a single type of fatty acyl chain or more than one type of fatty acyl chain, the only requirement being that such hydrolysis provides at least one unsaturated fatty acid substrate for an oleate hydratase. One or more purified triglycerides may be provided in the reaction medium such as commercially available triolein. However, more desirably one or more triglycerides may be provided as a component of a natural oil, oily waste product or oil-containing preparation derived therefrom.

For example, for this purpose a natural plant oil may be employed. Of particular interest for this purpose are plant oils comprising triacylglycerols known to contain a high percentage of a mono-unsaturated C18 fatty acid substrate for OHase, e.g. castor oil, corn oil, soybean oil, linseed oil, rapeseed oil, palm oil and sunflower oil. A number of plant oils comprise a high content of triacylglycerol containing oleic acid and may therefore be of particular use where it is desired to provide 10-HSA for estolide formation, e.g. olive oil, corn oil, linseed oil, canola oil, sunflower oil, soybean oil, peanut oil, pecan oil, macadamia oil, grape seed oil and sesame oil. The following oils with a relatively high amount of triolein/oleic acid have been chosen as a starting source of triglyceride by the inventors: olive oil (55-83% oleic acid), corn oil (20.0-42.2% oleic acid), linseed oil (14.0-40% oleic acid), sunflower oil (14-39.4% oleic acid), soybean oil (17-30% oleic acid), peanut oil (52-60% oleic acid) [Harwood et al. The Lipid Handbook with CD-ROM, 3rd edition, CRC Press 2007, pages 66-67].

Other natural oils of possible interest for biotransformation of triglyceride to estolide in accordance with the invention include oiticica oil and tall oil (a by-product of wood-pulp manufacture including resin acids and fatty acids including oleic acid). A starting triglyceride source such as a natural oil or oily waste product may provide monomers for the final lipase esterification step in addition to one or more hydroxy-FAs via lipase hydrolysis and OHase action. Nevertheless, to simplify the end products for initial proof of concept studies, use of commercially available triolein was preferred as illustrated by the following examples.

EXAMPLES

Figure 3:
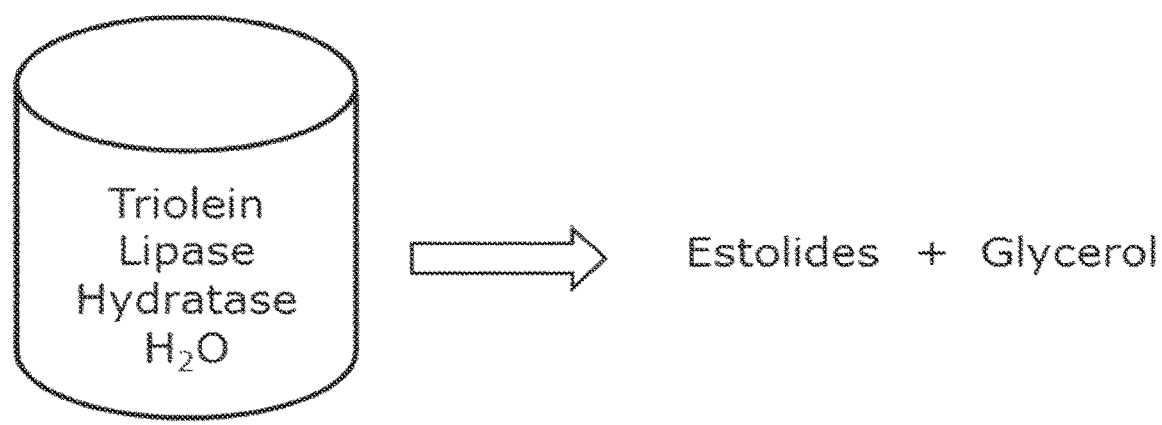
FIG. 3: Scheme for the conversion of triolein to one or more fatty acid estolides by a one pot enzymatic process of the invention. The reaction conditions shown correspond to the reaction conditions illustrated by the examples but may be varied provided the OHase and lipase both remain active.

The following examples 1 to 3 accord with the one-pot scheme shown in FIG. 3. Example 4 illustrates the same scheme in which triolein is substituted by a natural oil containing a high percentage of the same triglyceride.

Example 1: Synthesis of Monoestolide of 10-Hydroxystearic Acid with Oleic Acid in a One-Pot Conversion of Triolein Using a Lipase from *C. rugosa* and Oleate Hydratase from *Elizabethkingia meningoseptica*

Enzymes

The lipase from *Candida rugosa* was obtained from Fluka. The hydrolytic activity of the lipase was determined as 0.05 U/mg using p-nitro-phenyl palmitate as substrate. One unit will hydrolyse one micromole of p-nitrophenol per minute from p-nitrophenol palmitate at 37° C. and pH 8.

Recombinant OHase of *E. meningoseptica* with an N-terminal His tag was obtained by using cell-free extract of *E. coli* TOP10 cells containing the plasmid pBAD-HISA-OH (Bevers et al. (2009) J. Bacteriol. 191, 5010-5012). The recombinant cells were grown at 37° C. in TB (Terrific Broth) medium supplemented with 100 μg ml$^{-1}$ ampicillin until the OD600 reached the value 0.6-0.8. The expression of the recombinant enzyme was induced by using arabinose to a final concentration of 0.02%, followed by incubation at 30° C., 180 rpm overnight. Cells were harvested by centrifugation (10,000 rpm, 30 min, 4° C.; Sorvall), washed with 20 mM Tris-HCl pH 8, and lysed in the same buffer with a cell disruptor at 1.5 kBar (Constant Systems, IUL Instruments). Cell free extract was separated from cell debris by centrifugation (4° C., 14,000 rpm, 30 min) and then filtered through a 0.45 μm filter. The enzyme was further purified by Ni-affinity chromatography (His-tag purification) using a HisTrap-HP column (GE Healthcare), and an FPLC system equipped with UV detection. The washing buffer during purification was 20 mM Tris-HCl, 50 mM NaCl, 5 mM imidazole, pH 8.0 and protein elution was achieved with a gradient up to 50% of the same buffer (20 mM Tris/HCl, 50 mM NaCl, 500 mM imidazole, pH 8.0). Pooled fractions were concentrated and desalted using a Viva spin ultrafiltration tube (10 kDa cutoff; Vivascience), and concentrated again to about 5-15 mg mL$^{-1}$ in 50 mM Tris-HCl buffer, pH 8.0. Stock solutions of the enzyme were stored at -20° C. Purification was monitored by SDS-PAGE. Oleate hydratase was identified as a 70 kDa protein band on SDS-PAGE. This is consistent with the known 646 amino acids of the protein plus the hexa-histidine tag.

The activity of the OHase was determined by using oleic acid (2 mM) as substrate in 500 μl 20 mM Tris-HCl, 150 mM NaCl, pH 8, by incubation at 30° C., 1000 rpm for 2 hrs. The reaction was stopped by addition of 50 μl HCl and the substrate and the product was recovered by three consecutive extractions with one volume of dichloromethane. After solvent evaporation, the fatty acids were derivatized by using bis(trimethylsilyl) trifluoroacetamide/trimethyl-chlorosilane (BSTFA), and analyzed by GC-MS. The determined OHase activity was 104.76 U/g protein. One unit is the amount of enzyme converting one micromole of oleic acid per minute, at 30° C. and at pH 8.

Earlier studies on the effect of NaCl concentration at 0 to 200 mM on the activity of the OHase confirmed that NaCl was important for activity. Activity was observed at all NaCl concentrations tested (50 mM, 100 mM, 150 mM and 200 mM) but was optimal at 150 mM NaCl. Therefore, 150 mM NaCl was employed in all future reaction media for exemplification of the invention.

Reaction Process

Reaction mixtures containing lipase from *Candida rugosa* (10 mg/ml), oleate hydratase (0.2 mg/ml) and 10 mM triolein in 20 mM phosphate buffer 150 mM NaCl, pH 6.5 were incubated at 30° C., 1000 rpm for 24 hrs. The reaction was stopped by the addition of 50 μl HCl 2N and the substrate and products were extracted three times by using one volume of dichloromethane. The solvent was evaporated at 40° C. and the product was analyzed by GC-MS and MALDI-TOF MS.

Figure 5:
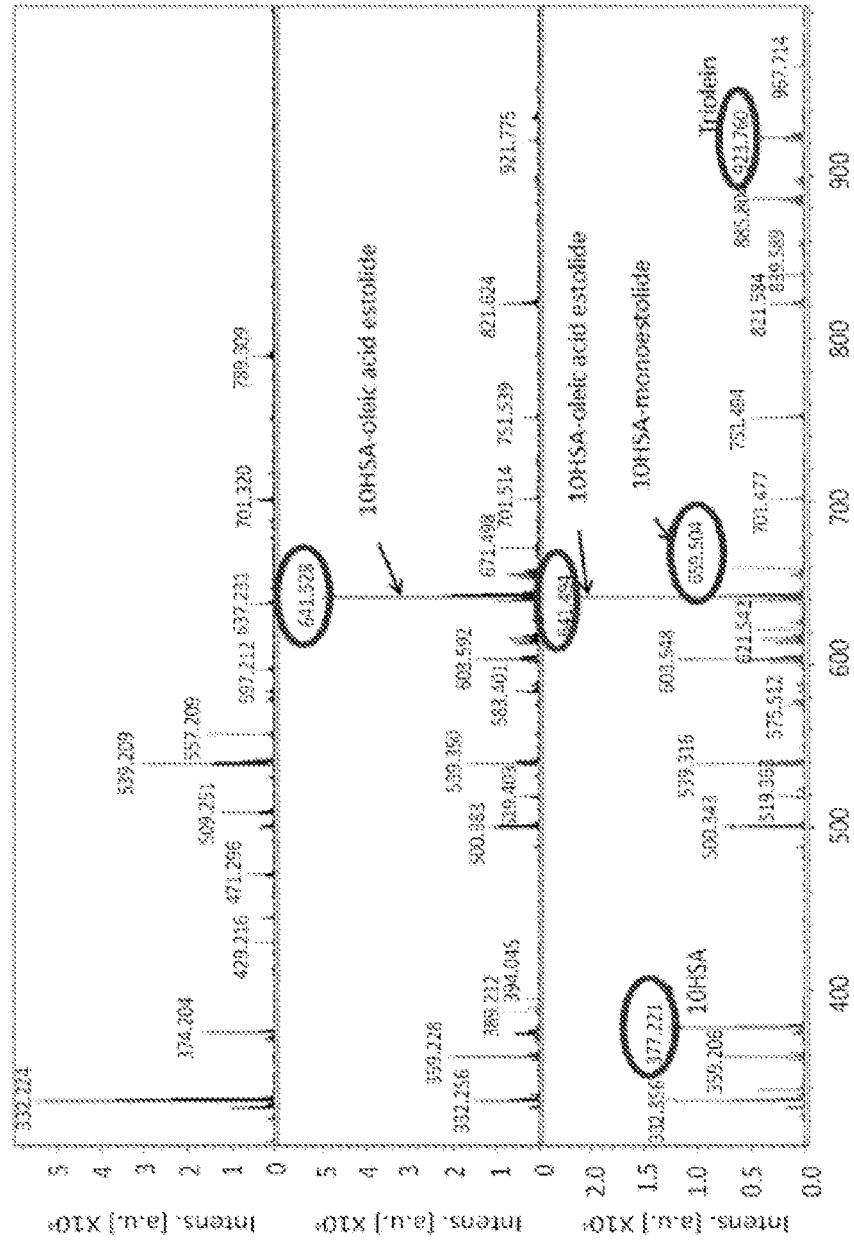
FIG. 5: MALDI-TOF-MS spectral analysis of the ester products obtained by carrying out a one-pot enzymatic process of the invention starting with triolein; (top trace) the matrix; (middle trace) the solvent extracted ester products obtained by the process of Example 1; (bottom trace) the solvent extracted ester products obtained by the process of Example 2.

MALDI-TOF-MS analysis identified the monoestolide of 10-hydroxystearic acid with oleic acid as the only product of the reaction, illustrated by the peaks corresponding to the masses of molecular adducts [M-K]$^+$, m/z: 603.04 found 603.59 and [M-2K]$^+$, m/z: 641.14 found 641.22 (see FIG. 5; middle trace). Glycerol was detected by GC-MS. Total conversion of triolein was achieved, as well as total conversion of the 10-HSA obtained by OHase-catalyzed hydroxylation of the liberated oleic acid.

As a negative control, the same reaction was carried out using only lipase from *Candida rugosa* (10 mg/ml) and without oleate hydratase. The product of the control reaction contained only oleic acid produced from triolein by enzymatic hydrolysis. The product did not contain 10-hydroxystearic acid or the monoestolide of 10-hydroxystearic acid with oleic acid.

Example 2: Synthesis of Monoestolides of 10-Hydroxystearic Acid in a One-Pot Conversion of Triolein Using a Lipase from *P. fluorescens* and Oleate Hydratase from *Elizabethkingia meningoseptica*

Enzymes

Lipase of *Pseudomonas fluorescens* was obtained from Sigma-Aldrich, and had a catalytic activity of 0.11 U/mg. One unit will hydrolyse one micromole of p-nitrophenol per minute from p-nitrophenol palmitate, at 37° C. and pH 8.

Recombinant oleate hydratase was employed as in Example 1.

Reaction Process

Reaction mixtures containing lipase from *Pseudomonas fluorescens* (5 mg/ml), oleate hydratase (0.2 mg/ml) and 10 mM triolein in 20 mM phosphate buffer 150 mM NaCl, pH 6.5 were incubated at 30° C., 1000 rpm or 48 hrs. The reaction was stopped by the addition of 50 μl HCl 2N and the substrate and products were extracted three times by using one volume of dichloromethane. The solvent was evaporated at 40° C. and the extracted substrate and product were analyzed by GC-MS and MALDI-TOF MS.

MALDI-TOF-MS analysis identified the monoestolide of 10-hydroxystearic acid with oleic acid ([M-K]$^+$, m/z: 603.04, found 603.31 and [M-2K]$^+$, m/z: 641.14, found 641.49) and the monoestolide of 10-hydroxystearic acid with itself ([M-K]$^+$, m/z: 621.04, found 621.54 and [M-2K]$^+$, m/z: 659.14, found 659.56), as reaction products (FIG. 5; bottom trace). Traces of triolein ([M-K]$^+$, m/z: 923.53, found 923.76) and some unreacted 10-hydroxyoleic acid (([M-K]$^+$, m/z: 376.68, found 377.22) were also identified.

As a negative control, the same reaction was carried out using only lipase from *Pseudomonas fluorescens* (5 mg/ml) and without oleate hydratase. The product of the control reaction contained only oleic acid produced from triolein by enzymatic hydrolysis and a small amount unreacted triolein. The product did not contain 10-hydroxystearic acid, the monoestolide of 10-hydroxystearic acid with oleic acid or the monoestolide of 10-hydroxystearic acid with itself.

Figure 6:
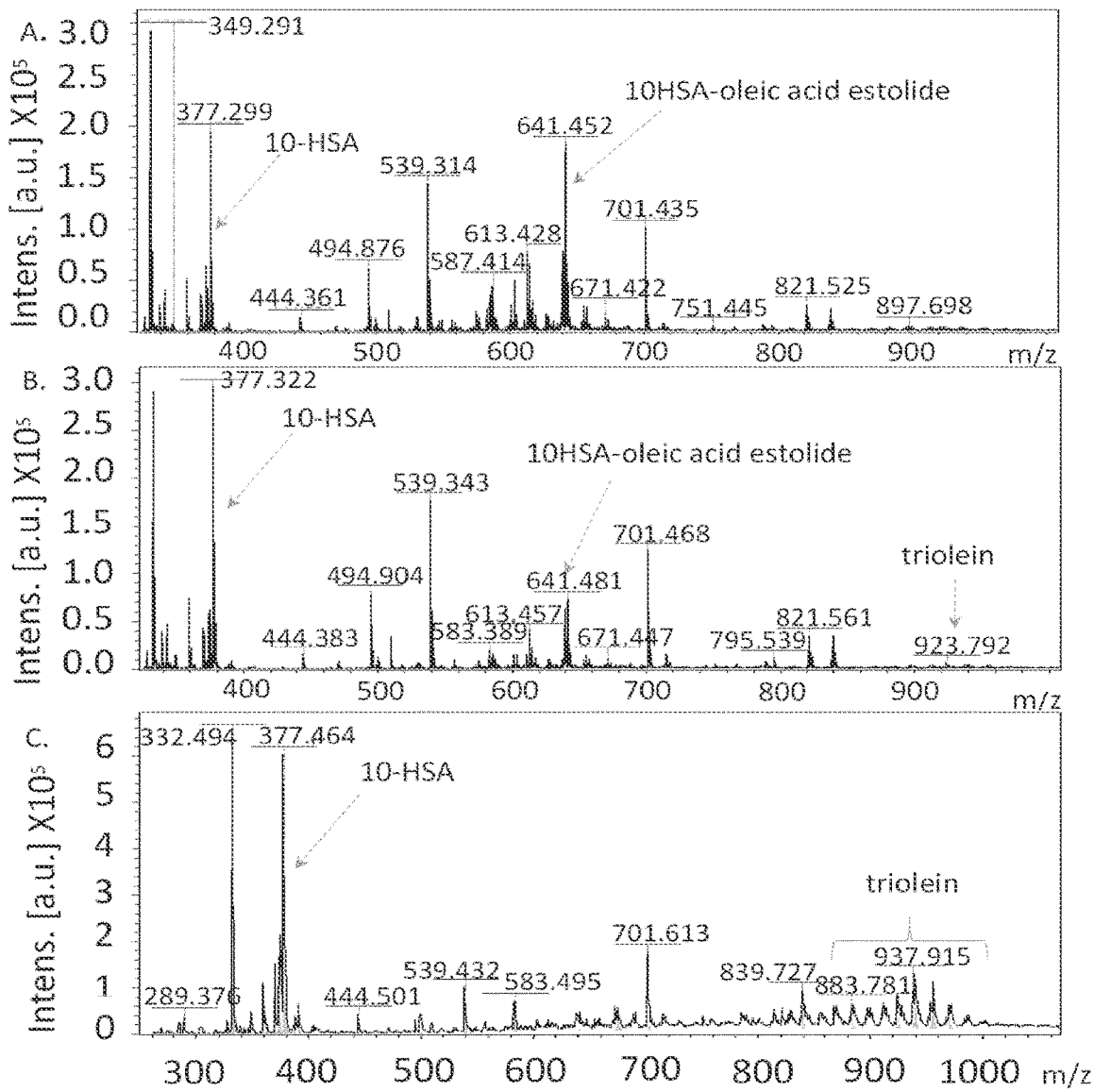
FIG. 6: MALDI-TOF-MS spectral analysis of the ester products obtained by carrying out a one-pot enzymatic process of the invention starting with triolein with 2 mg/ml oleate hydratase and *Candida rugosa* lipase at the following concentrations: (A) 2 mg/ml; (B) 0.2 mg/ml; (C) 0.04 mg/ml (Example 3).

Example 3: Biotransformation of Triolein to Estolides at Different Ratio Lipase/Oleate Hydratase Reaction mixtures containing triolein (14.3 mM, 12.4 mM and 13.2 mM) in 20 mM phosphate buffer 150 mM NaCl, pH 6.5 were treated with oleate hydratase from *Elizabethkingia meningoseptica* (2 mg/ml) and various amounts of lipase from *Candida rugosa*, e.g. 2 mg/ml, 0.2 mg/ml and 0.04 mg/ml. The mixtures were incubated at 30° C., 1000 rpm for 24 hrs. The reactions were stopped by the addition of 50 µl HCl 2N and the substrate and products were extracted three times by using one volume of dichloromethane. The solvent was evaporated at 40° C. and the extracted substrate and product were analyzed by GC-MS and MALDI-TOF MS. The results are summarised in Table 1 and FIG. 6. As seen in Table 1, the ratio between the activity of the lipase and the activity of oleate hydratase utilised has a large effect on the overall conversion of triolein and the yield of estolide. No estolide was formed at very low lipase/oleate hydratase ratio, although 58% of the oleic acid produced from triolein by hydrolysis was converted into 10-HSA.

TABLE 1

Results of the triolein conversion at different ratios between lipase from C. rugosa and oleate hydratase from E. meningoseptica (2 mg/ml)

| Added lipase (mg/ml) | Lipase/OHase weight | Lipase/OHase activity | Total conversion oleic acid (%) | Oleic acid conv. in 10 HSA (%) | 10HSA conv. in 10HSA-oleic acid estolide (%) | Triolein conversion (%) |
|---|---|---|---|---|---|---|
| 2 | 1 | 0.48 | 81.0 | 56.8 | 42.4 | >98 |
| 0.2 | 0.1 | 0.05 | 79.2 | 50.7 | 36.4 | 90 |
| 0.04 | 0.02 | 0.01 | 58.0 | 58.0 | 0 | 32 |

Example 4: Biotransformation of Olive Oil to Estolides in a One-Pot Conversion Using a Lipase from *C. rugosa* and Oleate Hydratase from *Elizabethkingia meningoseptica*

Reaction mixtures containing 21.4 mg/ml of olive oil consisting of approximately 84% triolein in 20 mM phosphate buffer 150 mM NaCl, pH 6.5 were treated with oleate hydratase from *Elizabethkingia meningoseptica* (2 mg/ml) and lipase from *Candida rugosa* (2 mg/ml). The mixture was incubated at 30° C., 1000 rpm for 24 hrs. The reaction was stopped by the addition of 50 µl HCl 2N and the substrate and products were extracted three times by using one volume of dichloromethane. The solvent was evaporated at 40° C. and the extracted substrate and product were analyzed by GC-MS and MALDI-TOF MS.

High conversion of the triolein component of olive oil was obtained. Oleic acid and 10-HSA were determined by GC analysis at a molar ratio of 40:60, showing a high conversion of oleic acid under the action of oleate hydratase. Formation of the monoestolide of 10-HSA capped with oleic acid was identified in MALDI-TOF-MS spectra. No products of the reactions (i.e. 10-HSA and estolides) were found by GC and MALDI-TOF-MS analysis of control reactions without enzymes.

As indicated above, olive oil may be substitute in the protocol by other oils with a high amount of triolein/oleic acid including sunflower oil, soybean oil, peanut oil, linseed oil and corn oil.

Example 5: Lipase Formation of Esters from 10-HSA a) Screening for Lipases for Estolide Synthesis Enzymes:

The following lipases were screened: Amano lipase from *Pseudomonas fluorescens* (*P. fluorescens*; 0.11 U/mg), *Pseudomonas cepacia* (*P. cepacia*; 0.37 U/mg), *Thermomyces lanuginosus* (*T. lanuginosus*; 1.09 U/mg), and CLEA Alcalase were purchased from Sigma Aldrich. The lipases from *C. rugosa* (0.05 U/mg), *Aspergillus oryzae* (*A. oryzae*; 1.30 U/mg), *Candida antarctica* A (*C. antarctica* A; 0.02 U/mg), *Rhizopus arrhizus* (*R. arrhizus*; 0.01 U/mg), *Penicillium roqueforti* (*P. roqueforti*; 0.01 U/mg), *Mucor javanicus* (*M. javanicus*; 0.16 U/mg), *Candida lipolytica* (*C. lipolytica*; 2.59 U/mg), *Thermanaerobium brockii* (*T. brockii*; 1.31 U/mg) were obtained from Fluka. Novozyme 435, Lipozyme TL, *Candida antarctica* B (*C. antarctica* B) lipase were purchased from Novozymes. The lipases from *Alcaligenes* sp (lipase TL; 3.86 U/mg), *Pseudomonas stutzeri* (*P. stutzeri*; 1.21 U/mg) (Lipase TL), were products of Meito Sangyo Co. Ltd, Japan. The CLEA from *C. antarctica* B and *P. stutzeri* were purchased from CLEA Technologies. One unit will hydrolyse one micromole of p-nitrophenol per minute from p-nitrophenol palmitate, at 37° C. and pH 8.

Process:

The reactions were performed by adding native and immobilized lipases, 50 U/mmol substrate, to a 1 mM solution of 10-hydrostearic acid brought to a final volume of 1 ml in toluene, at 60° C. at 350 rpm for 24 h. At the end of the reaction the enzyme was removed by centrifugation (13,000 rpm, 3 min), and the reaction mixture was analyzed by GC-MS and MALDI-TOF MS.

The reaction product was derivatized with BSTFA+TMCS (99:1), at 2:1 reagent: sample ratio (w/w), for 1 h at 95° C., and analyzed by GC-MS, using hexadecane as internal standard. For the calculation of conversions, the concentration of each substrate was determined based on a calibration curve in the range from 0.05 mM to 3 mM, using hexadecane as internal standard. For the MALDI-TOF MS analysis, samples were mixed with trans-2-[3-(4-t-butyl-phenyl)-2-methyl-2-propenylidene]malononitrile (DCTB) matrix and potassium trifluoroacetate (KTFA) as ionization agent. 10 µL of the sample was mixed with 10 µL of matrix solution (40 mg/mL DCTB solubilized in THF) and 3 µL of KTFA (5 mg/mL). About 0.3 µL of the mixture was applied on the plate and measured in the positive mode.

The results given in Table 2 show that all lipases tested, except the lipase from *P. cepacia*, are able to convert 10-HSA into the corresponding monoestolide (ME). Lipases from *A. oryzae, C. antarctica* A, *C. rugosa* and *P. fluorescens* produced small amounts of cyclic diester (CDE) in low amounts, ranging from 1.2% (*A. oryzae*) to 10% (*P. fluorescens*). The lipase from *P. stutzeri*, both free and immobilized, produced low amounts of longer estolides, e.g. diestolides (DE) and triestolides (TE). Highest 10-HSA conversion was obtained with immobilized enzymes, most probably due to the increased stability.

TABLE 2

Synthesis of estolides from 10HSA using free and immobilized lipases

| Lipase | 10HSA conversion | Product type (MALDI) |
|---|---|---|
| *Free enzymes* | | |
| Alcaligenes PL | 52.5 | ME, CDE |
| A. oryzae | 21.4 | ME, CDE |
| C. antarctica A | 15.9 | ME, CDE |
| C. antarctica B | 21.4 | ME |
| C. lipolytica | 21.5 | ME |
| C. rugosa | 18.4 | ME, CDE |
| M. javanicus | 12.9 | ME |
| P. cepacia | 0.0 | Not found |
| P. fluorescens | 25.3 | ME, CDE |
| P. stutzeri | 34.4 | ME, DE |
| P. roqueforti | 3.1 | ME |
| R. arrhizus | 9.6 | ME |
| T. brockii | 31.9 | ME |
| T. lanuginosus | 9.2 | ME |
| *Immobilized enzymes* | | |
| Lipozyme | 57.3 | ME |
| Novozym 435 | 65.7 | ME |
| CLEA CalB | 65.1 | ME |
| CLEA P. stutzeri | 66.5 | ME, DE, TE |
| CLEA Alcalase | 35.3 | ME |

TABLE 3

Conversion of 10-HSA with lipase from *P. fluorescens* and *P. stutzeri* in buffer of different pH values, at 40 and 60° C.

| | 40° C. | | | 60° C. | | |
|---|---|---|---|---|---|---|
| | 10HSA | Product | | 10HSA | Product | |
| pH | conv. (%) | type | Mw/PDI | conv. (%) | Mw/PDI | PD |
| *P. fluorescens* lipase | | | | | | |
| 4 | 28 | ME (82%), DE (18%) | 715/1.03 | 70 | 1639/1.16 | 2-15 |
| 6.5 | 18 | ME (62%), DE (32%) | 733/1.03 | 68 | 1713/1.15 | 2-9 |
| 8 | 5 | ME | 633/1 | 31 | 1514/1.15 | 2-9 |
| *P. stutzeri* lipase | | | | | | |
| 4 | 0 | 0 | 0 | 25 | 1645/1.18 | 2-12 |
| 6.5 | 0 | 0 | 0 | 43 | 1187/1.14 | 2-7 |
| 8 | 0 | 0 | 0 | 8 | 853/1.07 | 2-4 |

ME: monoestolide,
DE: diestolide,
TE: triestolide;
Mw: average molecular weight (g/mol),
PDI: polydispersity index;
PD: degree of polylmerisation b) Synthesis of Estolides by Lipase-Catalyzed Conversion of 10-Hydroxystearate in Aqueous Phase at Different Temperatures Enzymes: Lipase from *Pseudomonas fluorescens* (*P. fluorescens*; 0.11 U/mg, obtained from Sigma) and lipase from *Pseudomonas stutzeri* (*P. stutzeri*; 1.21 U/mg, obtained from Meito Sangyo Co. Ltd, Japan) were used in these experiments. One unit will hydrolyse one micromole of p-nitrophenol per minute from p-nitrophenol palmitate, at 37° C. and pH 8.

Reaction: To a suspension of 15 mM 10-hydroxystearic acid in 20 mM phosphate buffer of at a given pH, e.g. pH 4, pH 6.5 or pH 8, 100 µl of enzyme solution were added, to an enzyme concentration of 50 U/mmol substrate. The total volume of the reaction mixture was 1 ml. The reaction mixture was stirred at 350 rpm for 24 h. Reactions were carried out at 40° C. and 60° C. respectively. As a negative control, the same reaction was carried out at identical conditions but without the addition of the enzyme. At the end of the reaction the enzyme was removed by centrifugation (13,000 rpm, 3 min), and the reaction mixture was analyzed by GC-MS and MALDI-TOF MS.

Figure 7:
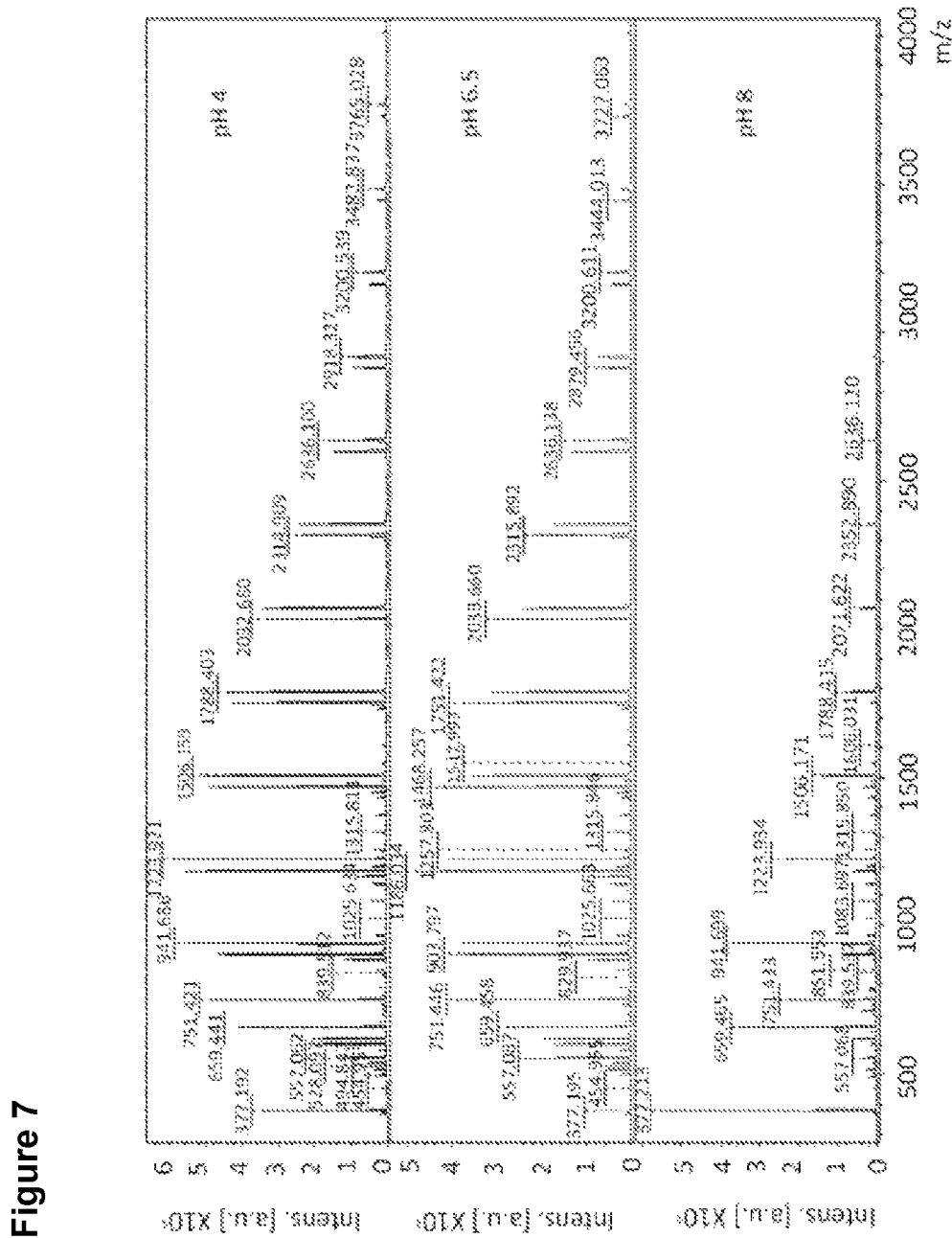
FIG. 7: MALDI-TOF-MS spectra of estolides obtained from 10-HSA with lipase from *P. fluorescens* in aqueous phase at 60° C. and pH 4, pH 6.5 and pH 8, respectively.

Samples were treated prior to analysis as described in Example 5a. FIG. 7 gives the MALDI-TOF-MS spectra of the products produced at acidic pH values. The MALDI-TOF-MS spectra of control reactions contained only the mass corresponding to the substrate 10-HSA ([M-K$^+$], m/z: 377.04). The results in Table 3 show the increase of 10-HSA conversion into estolides as well as the formation of longers estolides [the estolides ranged from monoestolides (i.e. dimers) to E14 (i.e. 15-mers)] with increasing temperature from 40 to 60° C. at acidic pH values, e.g. pH 4 and pH 6.5. Low temperatures, e.g. 40° C. and pH 6.5 are favourable for the production of monoestolides of 10-HSA as a sole product.

Example 7: Hydration of Oleic Acid with Oleate Hydratase from *E. meningoseptica*

10-hydroxystearic acid was obtained by hydration of oleic acid using oleate hydratase from *E. meningoseptica*. 5 ml of cell free extract of OHase expressed in *E. coli* TOP10 cells (48 mg/ml total protein content) were added to an emulsion containing 0.6% (v/v) oleic acid in 20 mM Tris-HCl buffer, pH 8.0 and the mixture was incubated at 30° C. at 200 rpm for 12 h (total volume 50 ml). The reaction was terminated by addition of 100 µl of 4 N HCl 4 N (final pH 1-2), and the product 10-HSA that separates from the mixture as a white precipitate, was isolated by filtration, dissolved in acetone and isolated after solvent removal under vacuum (475 mg, 1.55 mmol, 10HSA yield 96%, purity >99%, as determined by GC, GC-MS and NMR).

Example 8: Increasing Operational and Thermal Stability of Oleate Hydratase by Immobilization Recombinant oleate hydratase (OHase) of *Elizabethkingia meningoseptica*, expressed in *E. coli* and purified as described above, was immobilized by different immobilization strategies including adsorption, crosslinking, entrapment and covalent bonding. Among the tested immobilization methods, covalent binding onto magnetic chitosan composite particles was most efficient; immobilization yields higher than 90% and recovered activities of up to 24% were achieved by covalent binding onto such composite particles. This is a good result for such a difficult and unstable enzyme. The resulting biocatalysts were further characterized in detail in terms of stability and reusability. The thermal stability was enhanced after immobilization. The OHase immobilized on magnetic chitosan composite particles retained more than 65% of its original activity after incubation at 50° C. for 2 hours, while the native enzyme was completely inactivated. Importantly, it was also surprisingly found that immobilization of the OHase on magnetic chitosan composite particles resulted in a radical improvement of operational stability of the OHase, as the covalently bound enzyme preserved 75% of the initial activity after five reuses. This renders such immobilized OHase of particular interest for commercial application of one-pot methods of the invention.

As noted above, an important concern for using isolated OHase for industrial purposes has been its low stability, even at ambient temperatures. As no straightforward approach for establishing a good immobilization method for a specified enzyme is known, this has to be determined experimentally by trial (Liese & Hilterhaus (2013), Chem. Soc. Rev. 42, 6236-6249).

Immobilization Methods

Chemicals

Oleic acid 96%, chitosan 85% deacetylated, amino-terminated magnetic particles (AMP), glutaraldehyde 50%, carboxyl terminated magnetic particles (CMP), fluorescein isothiocyanate (FITC), Span 80 (sorbitane oleate), bis(trimethylsilyl)trifluoroacetamide/trimethyl-chlorosilane (BSTFA+TMCS=99:1) were purchased from Sigma Aldrich. The standard grade Sepabeads EC-EP were kindly provided by Resindion S.R.L. (Italy), Ni-NTA Superflow resin was purchased from Qiagen, Celite 545 was obtained from Merck. Silane precursors dimethyldimethoxysilane (DMeDMeOS, 96%), tetraethoxysilane (TEOS, 98%) were purchased from Fluka Chemie GmbH (Buchs, Switzerland). Isobutyl trimethoxysilane (iBuTMOS, 97%) and (3-aminopropyl)trimethoxysilane (3-$NH_2$PrTMOS, 97%) were obtained from Sigma Aldrich (Steinheim, Germany), while tetramethoxysilane (TMOS, 99%) was obtained from Acros Organics (Geel, Belgium).

Activity Assay

Activities for the free and immobilized OHase were determined by using oleic acid (2 mM) as substrate in 500 µl 20 mM Tris buffer, 150 mM NaCl, pH 8, by incubation at 30° C., 1000 rpm for 2 hrs. The reactions were stopped by addition of 50 µl HCl 3N and the substrate and the product were recovered by three consecutive extractions with one volume of dichloromethane. After solvent evaporation, the fatty acids were derivatized by using BSTFA (Hudson et al. (1995) Appl. Microbiol. Biotechnol. 44, 1-6) and analyzed by GC-MS. The separation was carried out on Interscience Trace GC Ultra GC+PTV with AS3000 II autosampler equipped with Restek Rxi-5 ms 30 m×0.25 mm×0.25 µm capillary column, using the following conditions: oven temperature: 100-300° C. with 10° C. min-1 heating rate, injector temperature 300° C., carrier gas (helium) flow 1.0 mL min-1. Hexadecane was used as internal standard. Mass spectra were obtained from an Interscience Trace DSQ II XL quadrupole mass selective detector (El, mass range 35-500 Dalton, 150 ms sampling speed), mass spectrometer operated at 70 eV.

The specific activity was expressed as the amount of 10-HSA (µmol) formed by 1 g of enzyme protein in 1 min.

The recovered activity was defined as % ratio of the total activity of the immobilized enzyme and the total activity of the native enzyme used for immobilization.

Immobilization Method 1: Absorption 20 mg Celite 545 were mixed with 500 µL of OHase solution (2.87 mg ml-1) in 20 mM phosphate buffer, pH 8. The mixture was shaken at 4° C. for 48 h. The adsorbed Celite-OHase was separated by centrifugation and washed five times with 20 mM phosphate buffer pH 8 and two times with 20 mM Tris buffer. The protein concentration was determined in each washing step (except the washes with Tris buffer) by using the Bradford assay. The Celite-OHase was stored in 20 mM TRIS buffer at 4° C. until further use. The immobilization in the presence of an emulsifier was carried out by the same procedure, adding 30 µl emulsifier (Span 80) in the immobilization solution.

Method 2: Ni-NTA Agarose Beads Immobilization 1 ml of OHase solution (2.5 mg ml-1) in 20 mM Tris buffer pH 8 were added to 200 µl Ni-NTA Superflow resin. The mixture was shaken at room temperature for 1.5 h, 100 µm. The resin was washed three times with Tris buffer and stored at 4° C. until further use.

Method 3: Ionic Binding on Chitosan

500 µl of 20 mM phosphate buffer, pH 6.5, were added to 25 mg chitosan, and the suspension was shaken at room temperature for 3 h, 100 rpm. The wet chitosan was separated from buffer solution by centrifugation at 14,000 rpm for 10 min, 500 µl OHase solution in 20 mM phosphate buffer pH 6.5 (2.5 mg ml-1) were added and the mixture was shaken at 4° C., 100 rpm for 24 hrs. The washing step was performed as described for method 1.

Covalent Binding onto Different Supports

Sequence analysis of OHase reveals a high density of 50 Lys groups which can be involved in covalent binding with various activated supports.

Method 4a: Epoxy-Sepabeads

25° C./4° C. 900 µl OHase solution (1.15 mg ml-1) in 50 mM phosphate buffer pH 8 were added to 100 mg immobilization support activated with epoxy groups. The mixture was incubated overnight at 100 rpm, 24 h, at 4° C. and 25° C., respectively. A set of experiments were performed by treating with 3M glycine solution in 20 mM phosphate buffer pH 6.5, overnight at 4° C., 100 rpm, in order to block all free epoxy groups. The epoxy-sepabeads were removed from the mixture by filtration, washed as described for method 1 and stored at 4° C. until further use.

Method 4b: 4° C.-Three Steps

OHase immobilization in three steps was performed as previously described by Mateo et al. (2002) Biotechnol. Prog. 18 629-634 at pH 7 in 1 M sodium phosphate for 24 hrs, followed by incubation of the immobilized enzyme at pH 9 in 100 mM sodium phosphate for 72 h and hydrophilization of the support surface by incubating the derivative for 24 hrs at pH 8.5 in the presence of 3 M glycine.

Functionalized Magnetic Particles (Amino Terminated, Carboxyl Terminated)

Method 5a: Amino-Terminated Magnetic Particles (AMP)

200 µl AMP suspension, containing magnetic iron oxide particles approximately 1 µm in size, were activated three times by using coupling buffer (0.01 M pyridine in distilled water pH 6, adjusted with 2N HCl) to a final volume of 1 ml and vigorous shaking. The supernatant was aspirated and 400 µl of 5% glutaraldehyde solution were added. The particles were re-suspended and gently shaken at room temperature for 3 hrs. The supernatant was aspirated and the wet cake was washed three times in order to eliminate the unreacted glutaraldehyde. 300 µl of OHase solution (5.74 mg ml-1 in 20 mM phosphate buffer, pH 8) were added to the glutaraldehyde-activated particles and after re-suspension of the particles the mixture was gently shaken at 4° C. for 48 hrs. The particles were then separated magnetically and re-suspended in 500 µl of Glycine Quenching solution (1.0 M in distilled water pH 8, adjusted with 2N NaOH), for 30 min at room temperature, 100 rpm. At the end a washing step was performed three times by washing buffer (0.01 M Tris base containing 0.15 M NaCl, 0.1% (w/v) bovine serum albumin, 0.001 M EDTA sodium salt and 0.1% (w/v) sodium azide), and three times by 20 mM Tris buffer, pH 8. The immobilized enzyme was stored at 4° C. in 20 mM Tris buffer, pH 8.

Method 6: Carboxyl-Terminated Magnetic Particles (CMP)

250 µl CMP suspension were activated 3 times by using coupling buffer (0.01 M phosphate buffer with 150 mM NaCl in distilled water, pH 5.5, adjusted with 2N HCl) to a final volume of 0.5 ml and shaking vigorously. The particles were re-suspended in 250 µl coupling buffer, 100 µl coupling agent (1-ethyl-3(3-dimethylaminopropyl) carbodiimide EDCl, ~0.6 mg ml-1), 250 µl OHase solution in phosphate buffer (5.74 mg ml-1) were added, and the mixture was gently shaken at 4° C. for 48 hrs. Washing and storing conditions were the same as with AMP (see above).

Method 7: Covalent Binding on Pre-Activated Chitosan (CHT-GL)

400 µl glutaraldehyde 25% were added to 25 mg chitosan in 1.6 ml 20 mM phosphate buffer, pH 6.5. The suspension was shaken at room temperature for 3 h, 100 rpm. The glutaraldehyde activated chitosan was washed three times with 2 ml 20 mM phosphate buffer pH 7. 500 µl OHase solution (2.5 mg ml-1) was added and the mixture was shaken at 4° C., 100 rpm, for 24 hrs. The washing step was performed as described for method 1.

Method 8: Covalent Binding on Magnetic Chitosan Composite Particles (AMP-CHT).

Magnetic chitosan composite particles, in which amino-terminated magnetic particles (AMP) as described above are dispersed in a chitosan matrix (see FIG. 8), were prepared as described by Kumar et al. (2013) Biotechnol. Bioprocess Eng. 787-795) with some modifications. Chitosan 2% (w/v) solution in acetic acid (2%) was added to 187.5 mg wet AMP in 5:1 ratio (w/w). The mixture was vigorously shaken and kept 1 hr in a sonication bath for complete homogenization. The macroparticles were precipitated into sodium hydroxide 1M solution containing 26% ethanol as described elsewhere [Biró et al. (2008) J. Biochem. Biophys. Methods 70, 1240-1246), washed with distilled water and stored at 4° C. until further use. Before immobilization, the particles were activated by adding 5% glutaraldehyde for 4 hrs at 10° C. in 20 mM phosphate buffer of pH 6.5. 250 µl OHase solution (2.5 mg ml-1) were added to 150 mg wet macroparticles, completed to a total volume of 1 ml with 20 mM phosphate buffer pH 7, and gently mixed overnight at 10° C. The immobilized enzyme was washed as previously described for method 1, and stored at 4° C. in 20 mM Tris buffer pH 8.

Method 9: Cross-Linked Enzyme Aggregates (CLEA)

250 µl OHase solution (2.3 mg ml-1) was mixed with 750 µl saturated ammonium sulfate solution, adjusted to pH 8 with NaOH. The mixture was shaken at 500 rpm at 4° C. for 112.5 µl (0.3%, w/v) of 25% (w/v) glutaraldehyde was added drop wise into the tube and the mixture was shaken at 4° C., 500 rpm for 3 h. The CLEAs were removed by centrifugation (14,000 rpm, 30 min), washed three times with 20 mM phosphate buffer pH 8 and two times with 20 mM TRIS buffer, and stored in the same buffer until further use.

Method 10: Sol-Gel Entrapment

The OHase sol-gel entrapment has been performed mainly as the previously described method for subtilisin (Corici et al. (2011) J. Mol. Catal. B: Enzym. 73, 90-97). In a 4 ml glass vial OHase solution (195 µl, containing 5.87 mgml-1, in 20 mM Tris buffer pH 8), 1M NaF (25 µl), 4% PEG 20,000 solution (25 µl) and isopropyl alcohol (50 µl) were mixed (magnetic stirring, 600 rpm). 1.5 mmol of silane precursors in different molar ratio were added and the mixing continued at room temperature until the gelation started. The gel was kept 24 hrs at 4° C. to complete polymerization and then the bulk gel was washed to eliminate unreacted monomers and additives with Milli-Q water (2.5 ml), isopropyl alcohol (1.25 ml) and n-hexane (1.25 ml) and dried at 25° C. for 24 hrs. The sol-gel encapsulated enzyme was crushed in a mortar and stored at 4° C. until further use.

Influence of pH on OHase Activity

The effect of pH on native and immobilized OHase activity was evaluated in the pH range 4-9 in 9 steps, by using a broad range of pH buffer solutions containing citric acid, boric acid and trisodium phosphate buffer.

Influence of Temperature on OHase Activity

Incubation of the native/immobilized enzyme was carried out for 2 hrs in the absence of the substrate at different temperatures, in the 30-50° C. range, followed by cooling on ice for 10 min. The residual activity of the enzyme was then determined.

Reuse of the Biocatalyst

The activity of immobilized OHase was determined after repeated use of the biocatalyst at 30° C. for 2 hours per cycle. After each cycle, the immobilized enzyme was separated and washed with 20 mM Tris Buffer, 150 mM NaCl, pH 8, for 3 times. Fresh buffer and substrate were added, the activity of the reused biocatalyst was assayed and the obtained value was compared to the first run (defined as 100%).

Morphological Characterization of Immobilized OHase

The OHase protein was labelled with FITC (based on PIERCE EZ-Label™ FITC Labeling Kit). The coupling reaction of OHase with FITC was started by adding dropwise 600 µl of FITC (1 mg ml-1 dissolved in dimethylformamide) into the OHase solution (5.87 mg ml-1 in phosphate buffer pH 8). The mixture was incubated for 1 h at room temperature. The labelled OHase was separated from unreacted FITC by several washes with phosphate buffer 20 mM pH 8, using a centrifugal filter device (Centricon PL-30, with a membrane nominal molecular weight limit of 30,000 Da). UV-VIS spectra were collected after each washing step, until the absorbance at 493 nm (characteristic values of FITC) decreased up to 0.1 absorbance units. The protein concentration was determined by the Bradford assay. The FITC labelled protein was immobilized based on the method described for covalent binding on magnetic chitosan composite particles and the fluorescence micrographs were registered by a Leica True Confocal Scanner (Leica TCS SPE), with 10 fold spot magnitude.

Results and Discussion

The results are presented in Table 4 and are discussed in detail for each immobilization method in this section.

Adsorption:

Immobilization of OHase on Celite 545, a slightly hydrophobic support, resulted in low protein loading and low recovered activity. (Table 4, entry 1). The lack of activity could be attributed to the hydrophilic regions on the enzyme surface that lead to desorption in aqueous environment, surpassing the interaction between the hydrophobic part of the enzyme surface and the hydrophobic support. In fact, most of the enzymatic protein was recovered in the washing steps. By using Span 80 as additive during the immobilization process, the protein loading increased up to 3 times showing that the adsorption of the enzyme was more effective in the presence of an emulsifier, but the activity remained low.

Ionic Binding:

The ionic binding of OHase onto chitosan, an amino-functional polysaccharide with the pKa of the amino group of 6.5 was performed at this pH (i.e. 6.5) since the net charge of the enzyme calculated based on the amino acid sequence, is about −12.0. The protein loading value (Table 4, entry 4) exceeded 95%, but the specific activity of 11.8 U/g protein corresponds to only 5.5% recovered activity.

Affinity:

Because the recombinant OHase had a His-tag and Ni-affinity chromatography was used to purify the enzyme with high protein recovery, this method was also studied as an immobilization tool. The Ni-Superflow resin led to total binding of the enzyme, but unfortunately the immobilized enzyme showed very low specific activity and less than 5% of the initial activity was recovered (Table 4, entry 3). The results suggest that immobilization of His-tag enzymes by affinity is not universally applicable, although the method has been successfully used for immobilization of PikC hydroxylase (bacterial P450), p-nitrobenzyl esterase, benzaldehyde lyase and horseradish peroxidase.

Cross-Linked Enzyme Aggregates:

OHase CLEA obtained showed high specific activity compared with the physical immobilized enzyme (Table 4, entry 5), but the recovered activity did not exceed 17%.

Entrapment in Silica Sol-Gel Matrices:

This approach has been previously applied for the sol-gel entrapment of lipases designated to work in organic solvents as well as for isubtilisin and nitrile hydratase, which exhibited high enough. In the present study, the OHase was fully entrapped in all sol-gel preparations (Table 4, entries 12-15), but it did not show catalytic activity.

Covalent Binding:

The recovered activities (Table 4, entries 6-11) spanned over a wide range, between 1.0% and 23.7%, even if the immobilization protocols were performed under mild conditions. The covalent binding on epoxy sepabeads was performed at different temperatures in one or three steps, in order to avoid the loss of enzyme activity during the immobilization process. However, the use of epoxy-sepabeads as carrier for OHase (Table 4, entry 9 and 10) yielded less than 5% recovered activity. The recovered activity of OHase immobilized onto sepabeads was low, even when glycine was first used to block a part of the available reactive epoxy groups. Therefore, the drop in activity cannot be attributed solely to multipoint covalent attachment.

The results obtained when chitosan was used as support for OHase show the suitability of this natural support to accommodate the enzyme. See specific activity of 27.2 U/g, (Table 4, entry 8).

Covalent Binding of OHase on to Functionalized Magnetic Particles:

Recovered activities up to 20% corresponding to 42.5 U/g were obtained when carboxyl terminated magnetic particles were used as support, but some operational difficulties occurred during the magnetic separation of the immobilized enzyme, owing to the heterogeneity of the reaction system. The 10HSA product is a white solid and partial adsorption of this compound, as well as of the unreacted substrate on the surface of the magnetic particles could not be avoided. For this reason, modified magnetic particles, coated with a few atomic layers of chemically active polymer to provide functional groups for linkage were also studied. Chitosan was investigated as a suitable layer for magnetic particles on the basis of the experiments with chitosan noted above.

Magnetic Chitosan Composite Particles (AMP-CHT):

Using such particles as support and glutaraldehyde as linker, about 24% (about 51 U/g) of the initial activity was recovered following the immobilization. As noted above, this was considered a good result. The higher immobilization efficiency compared to other methods is due to the availability of numerous lysine groups near to the surface for covalent binding. The explanation of the partial loss of activity compared to the native enzyme could be the intramolecular linking of glutaraldehyde between lysine residues of the enzyme, or the possible mismatched orientation of the enzyme on the carrier caused by the presence of a Lys residue close to the entrance to the active site.

TABLE 4

Immobilization yield and recovered activity of OHase immobilized by different methods.

| Immobilization Method | Entry No. | Type of solid support | Protein loading [%] | Recovered activity [%] | Specific activity [U g protein$^{-1}$] |
|---|---|---|---|---|---|
| Adsorption | 1 | Celite 545 | 32.0 | 0 | 0 |
|  | 2 | Celite 545 + Span | 83.0 | 2.9 | 6.2 |
| Affinity | 3 | Ni-NTA Superflow resin | 99.3 | 1.8 | 3.9 |
| Ionic binding | 4 | CHT | 97.9 | 5.5 | 11.8 |
| Cross-linking | 5 | — | 99.8 | 16.5 | 35.4 |
| Covalent binding | 6 | AMP | 97.6 | ~2.0 | 4.3 |
|  | 7 | CMP | 98.4 | 19.8 | 42.5 |
|  | 8 | CHT-GL | 99.2 | 12.7 | 27.2 |
|  | 9 | Epoxy-SB: 25° C./4° C. | 99.5 | <1.0 | 2.1 |
|  | 10 | Epoxy-SB: 4° C. - three steps | 99.6 | ~2.0 | 4.2 |
|  | 11 | AMP-CHT | 99.3 | 23.7 | 50.8 |
| Sol-gel entrapment | 12 | TEOS/TMOS/TEOS:TMOS = 1 | 98.6 | 0 | 0 |
|  | 13 | TEOS:iBuTMOS = 1:1 | 98.4 | 0 | 0 |
|  | 14 | TEOS:DMeDMeOS = 1:1 | 98.7 | 0 | 0 |
|  | 15 | TEOS:3NH$_2$PrTMOS = 1:1 + 1: | 98.1 | 0 | 0 |

Effect of pH on the Catalytic Activity

Figure 9:
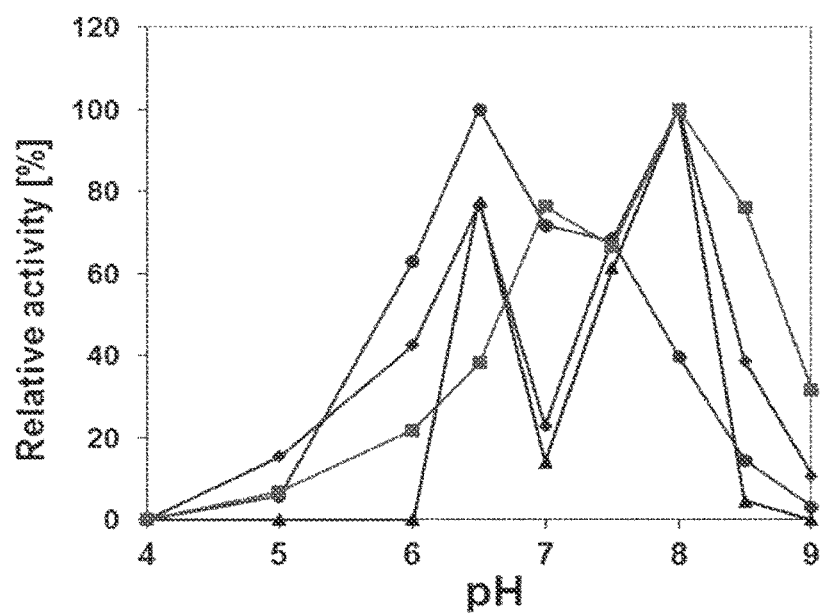
FIG. 9: pH profiles of native and covalently immobilized OHase (see Example 8): ▲ native OHase; ✦ OHase-CHT-GL; ✹ OHase-CMP; ✺ OHase-AMP-CHT

The effect of pH on the activity of native and immobilized enzyme was studied in the pH range 4.0-9.0 using the three most active covalently immobilized OHase preparations (AMP-CHT, CMP and CHT-GL); see FIG. 9. Two distinct maximum activity values for the native enzyme were found at pH 6.5 and 8.0. The same behaviour was observed using chitosan as the immobilization support. Such behaviour is usually due to the existence of two active isoenzymes that slightly differ in their structure, but this is not the case for OHase. An important modification of the pH profile occurred when both forms of functionalized magnetic particles were used as the immobilization support. These two preparations were active in a larger pH range compared to the native enzyme and their pH profile showed only one activity optimum, at pH 6.5 and pH 8.0 for OHase immobilized on CMP and AMP-CH, respectively. The most reasonable explanation of the occurrence of multiple peaks in the pH profile of OHase is the different physical state of the substrate, oleic acid, depending on the pH of the solution. At pH values less than 7, oleic acid is in the oil phase and the carboxylic groups are protonated. Above pH 7, an increase of ionization occurs and more structured lamellar systems or large vesicles of oleic acid are formed. It seems that both these forms are suitable to interact with the enzyme active site. The drop in the activity of the native enzyme at pH 7 is probably due to the lower reactivity of the non-ionized form of the substrate. In case of the enzyme immobilized on functionalized magnetic particles, interactions with the free carboxyl or amino groups still existing on the surface of the particles probably led to a certain extent of ionization even at pH 7 and increased the accessibility of the substrate for the hydration reaction.

Thermal Stability

Figure 10:
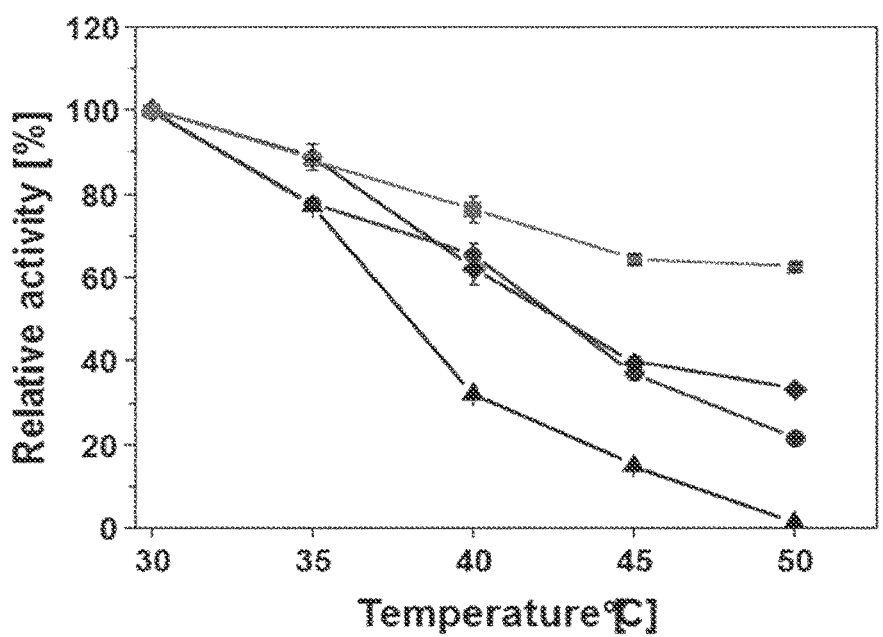
FIG. 10: Thermal stability of native and immobilized OHase (see Example 8): ▲ native OHase; ✦ OHase-CHT-GL; ✹ OHase-CMP; ✺ OHase-AMP-CHT

The thermal stability of the same OHase preparations was investigated; see FIG. 10. All immobilized OHases displayed better thermal stability compared to the native enzyme demonstrated by the higher values of activity at temperatures above 40° C. The highest relative activity value was achieved when AMP-CHT was used as support. The higher thermal stability can be attributed to the restricted flexibility of the enzyme after immobilization, rendering it more resistant to unfolding and denaturation. In the batch wise reaction, as noted above, the OHase immobilized on magnetic chitosan composite macroparticles retained more than 65% of its original activity after incubation at 50° C., while the native enzyme was completely inactivated. Such a significant improvement makes this enzyme available for utilization in a temperature range considered normal for biocatalytic processes, at sufficiently high reaction rates.

Repeated use of the immobilized OHase

OHase immobilized on magnetic chitosan composite particles was evaluated through several repetitive uses. After each cycle, the biocatalyst was recovered by magnetic separation, washed and recycled for 10-HSA production from oleic acid. Following acidification of the supernatant solution, the product and the unreacted raw material were extracted three times by dichloromethane. The activity of the first batch has been taken as reference. FIG. 11 shows the variation of immobilized OHase activity during multiple reuses by magnetic separation. As noted above, after five reaction cycles, the relative activity still remained about 75%, an excellent value taking into account the poor stability of the enzyme in the native form. Furthermore, in thinking about practical application, the reuse of the enzyme is considered to fully counteract the loss of activity during the immobilization.

Morphological Characterization of AMP-CHT Particles with Covalently Immobilized OHase The distribution of the immobilized enzyme on/in the magnetic chitosan composite particles was evaluated by labelling the OHase with fluorescein isothiocyanate (FITC) prior to the immobilization. The fluorescent layer on the external part of the sectioned chitosan composite particle indicated a uniform distribution of the immobilized OHase-FITC complex on the surface of the chitosan spheres. The inner part of the particles remained compact and did not contain immobilized enzyme. Hence, all enzyme molecules were available to be reached by 10-HSA substrate.

The invention claimed is:

1. A recombinant oleate hydratase (OHase) immobilized on a particulate support wherein said OHase has an N-terminal His tag covalently linked to glutaraldehyde-activated chitosan composite particles in which smaller magnetic iron oxide particles are dispersed in a chitosan matrix.

2. A recombinant OHase according to claim 1 wherein said magnetic iron oxide particles are amino-terminated magnetic particles.

* * * * *